US007674594B2

(12) United States Patent
Lee et al.

(10) Patent No.: US 7,674,594 B2
(45) Date of Patent: Mar. 9, 2010

(54) SCREENING ASSAY FOR INHIBITORS OF TRPA1 ACTIVATION BY A LOWER ALKYL PHENOL

(75) Inventors: Seunghun Paul Lee, Newtown, PA (US); Qifeng Yang, Belle Mead, NJ (US); Robert W. Bryant, Princeton, NJ (US); Tulu Buber, Newtown, PA (US)

(73) Assignee: Redpoint Bio Corporation, Ewing, NJ (US)

( * ) Notice: Subject to any disclaimer, the term of this patent is extended or adjusted under 35 U.S.C. 154(b) by 0 days.

(21) Appl. No.: 11/828,955

(22) Filed: Jul. 26, 2007

(65) Prior Publication Data
US 2008/0050750 A1    Feb. 28, 2008

Related U.S. Application Data

(60) Provisional application No. 60/833,481, filed on Jul. 27, 2006.

(51) Int. Cl.
G01N 33/53    (2006.01)
C07K 14/705   (2006.01)

(52) U.S. Cl. .................................. 435/7.1; 530/350

(58) Field of Classification Search .................. None
See application file for complete search history.

(56) References Cited

U.S. PATENT DOCUMENTS

| 4,399,216 | A |  | 8/1983 | Axel et al. |
| 5,010,175 | A |  | 4/1991 | Rutter et al. |
| 5,288,514 | A |  | 2/1994 | Ellman |
| 5,506,107 | A |  | 4/1996 | Cunningham et al. |
| 5,506,337 | A |  | 4/1996 | Summerton et al. |
| 5,519,134 | A |  | 5/1996 | Acevedo et al. |
| 5,525,735 | A |  | 6/1996 | Gallop et al. |
| 5,539,083 | A |  | 7/1996 | Cook et al. |
| 5,549,974 | A |  | 8/1996 | Holmes |
| 5,569,588 | A |  | 10/1996 | Ashby et al. |
| 5,593,853 | A |  | 1/1997 | Chen et al. |
| 6,188,965 | B1 |  | 2/2001 | Mayo et al. |
| 6,296,312 | B1 |  | 10/2001 | Congleton et al. |
| 6,403,312 | B1 |  | 6/2002 | Dahiyat et al. |
| 7,465,581 | B2 | * | 12/2008 | Bevan et al. ................ 435/325 |
| 2007/0082858 | A1 |  | 4/2007 | Steyger et al. |
| 2007/0196866 | A1 | * | 8/2007 | Patapoutian et al. ......... 435/7.2 |
| 2007/0219222 | A1 |  | 9/2007 | Moran et al. |
| 2008/0119412 | A1 |  | 5/2008 | Tymianski et al. |
| 2008/0124753 | A1 |  | 5/2008 | Lee et al. |
| 2009/0048194 | A1 |  | 2/2009 | Aerssens et al. |

FOREIGN PATENT DOCUMENTS

| WO | WO 91/19735 A1 | 12/1991 |
| WO | WO 92/00091 A1 | 1/1992 |
| WO | WO 93/09222 A2 | 5/1993 |
| WO | WO 93/20242 A1 | 10/1993 |
| WO | WO 94/12650 A2 | 6/1994 |
| WO | WO 95/31560 A1 | 11/1995 |
| WO | WO 96/10287 A1 | 4/1996 |
| WO | WO 01/25277 A1 | 4/2001 |
| WO | WO 2006/130806 A2 | 12/2006 |
| WO | WO 2007/098252 A2 | 8/2007 |
| WO | WO 2008/044660 A1 | 4/2008 |
| WO | WO 2008/129258 A1 | 10/2008 |

OTHER PUBLICATIONS

Xu et al., Nature Neuroscience, 9(5):628-635, May 2006.*
Lee et al., British Journal of Pharmacology, 153:1739-1749, 2008.*
Xiao et al., Journal of Neuroscience, 28(39):9640-51, 2008.*
Avenet, P., and Lindemann,B., "Perspectives of Taste Reception," *J. Membrane Biol.* 112:1-8, Springer-Verlag New York Inc. (1989).
Bandell, M., et al., "Noxious Cold Ion Channel TRPA1 is Activated by Pungent Compounds and Bradykinin," *Neuron* 41:849-857, Cell Press (2004).
Calixto, J.B., et al., "Contribution of natural products to the discovery of the transient receptor potential (TRP) channels family and their functions," *Pharmacol. Ther.* 106:179-208, Elsevier Inc. (May 2005).
Campbell, D.A., and Bermak, J.C., "Phosphonate Ester Synthesis Using a Modified Mitsunobu Condensation," *J. Org. Chem.* 59:658-660, American Chemical Society (1994).
Chen, C., et al., ""Analogous" Organic Synthesis of Small-Compound Libraries: Validation of Combinatorial Chemistry in Small-Molecule Synthesis," *J. Am. Chem. Soc.* 116:2261-2262, American Chemical Society (1994).
Cho, C.Y., et al., "An Unnatural Biopolymer," *Science* 261:1303-1305, American Association for the Advancement of Science (1993).
Clapham, D.E., et al., "International Union of Pharmacology. XLIII. Compendium of Voltage-Gated Ion Channels: Transient Receptor Potential Channels," *Pharmacol. Rev.* 55:591-596, The American Society for Pharmacology and Experimental Therapeutics (2003).
Dewitt, S.H., et al., "Diversomers: An approach to nonpeptide, nonoligomeric chemical diversity," *Proc. Natl. Acad. Sci. USA* 90:6909-6913, National Academy of Sciences (1993).
Dorsett, Y., and Tuschl, T., "siRNAs: Applications in Functional Genomics and Potential as Therapeutics," *Nature* 3:318-329, Nature Publishing Group (2004).
Eidelman, O., and Cabantchik, Z.I., "Continuous monitoring of transport by fluorescence on cells and vesicles," *Biochim. Biophys. Acta* 988:319-334, Elsevier Science Publishers B.V. (1989).

(Continued)

*Primary Examiner*—Marianne P Allen
(74) *Attorney, Agent, or Firm*—Sterne, Kessler, Goldstein & Fox PLLC

(57) ABSTRACT

The invention relates an assay useful for screening and identifying compounds as modulators of lower alkyl phenol activation of TRPA1. Thymol, a lower alkyl phenol anti-infective and the active ingredient in, e.g., mouthwashes, is stringent and has an objectionable burning taste sensation. Thymol activates the transient receptor potential like ion channel TRPA1. The assay described and claimed herein involves measurement of activation of TRPA1 and enables the screening of compounds that inhibit lower alkyl phenol, or thymol activation of TRPA1. Inhibitors of thymol activation of TRPA1 can be used to prevent the objectionable taste of thymol in medical uses where taste limits acceptance.

28 Claims, 12 Drawing Sheets

OTHER PUBLICATIONS

Figure 1A:
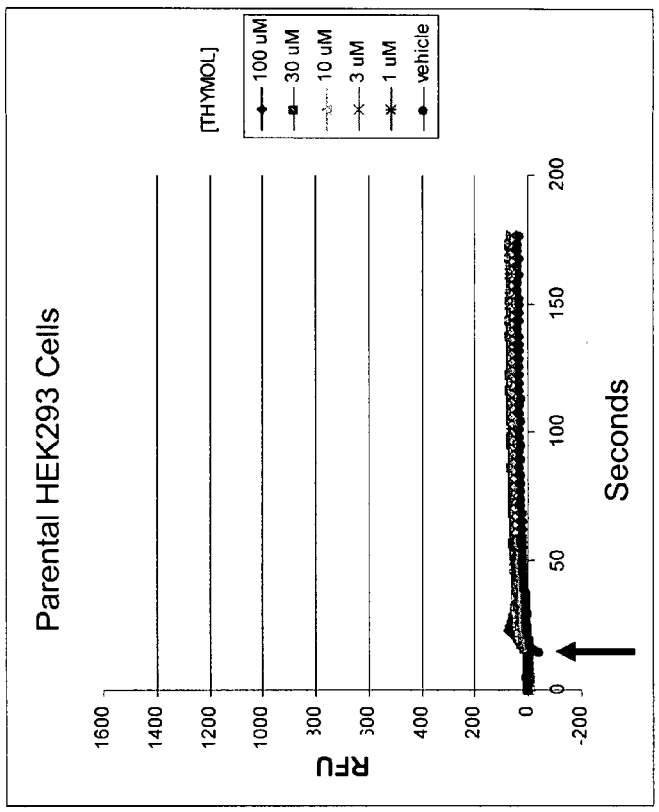

Epps, D.E., et al., "Characterization of the steady-state and dynamic fluorescence properties of the potential-sensitive dye bis-(1,3-dibutylbarbituric acid)trimethine oxonol (Dibac$_4$(3)) in model system and cells," *Chem. Phys. Lipids* 69:137-150, Elsevier Science Ireland Ltd. (1994).

Furka, Á., et al., "General method for rapid synthesis of multicomponent peptide mixtures," *Int. J. Pept. Prot. Res.* 37:487-493, Munksgaard International Publishers Ltd. (1991).

Gossen, M., and Bujard, H., "Tight control of gene expression in mammalian cells by tetracycline-responsive promoters," *Proc. Natl. Acad. Sci. USA* 89:5547-5551, National Academy of Sciences (1992).

Hagihara, M., et al., "Vinylogous Polypeptides: An Alternative Peptide Backbone," *J. Am. Chem. Soc.* 114:6568-6570, American Chemical Society (1992).

Hamill, O.P., and Sakmann, B., "Multiple conductance states of single acetylcholine receptor channels in embryonic muscle cells," *Nature* 294:462-464, Macmillan Journals Ltd. (1981).

Hirschammn, R., et al., "Nonpeptidal Peptidomimetics with a β-D-Glucose Scaffolding. A Partial Somatostatin Agonist Bearing a Close Structural Relationship to a Potent, Selective Substance P Antagonist," *J. Am. Chem. Soc.* 114:9217-9218, American Chemical Society (1992).

Hosford, D.A., et al., "A radiohistochemical measure of [$^3$H]TCP binding to the activated NMDA-receptor-gated ion channel in rat brain," *Brain Res.* 516:192-200, Elsevier Science Publishers B.V. (1990).

Houghten, R.A., et al., "Generation and use of synthetic peptide combinatorial libraries for basic research and drug discovery," *Nature* 354:84-88, Macmillan Magazines Ltd. (1991).

Jaquemar, D., et al., "An Ankyrin-like Protein with Transmembrane Domains Is Specifically Lost after Oncogenic Transformation of Human Fibroblasts," *J. Biol. Chem.* 274:7325-7333, The American Society for Biochemistry and Molecular Biology, Inc. (1999).

Jordt, S.-E., et al., "Mustard oils and cannabinoids excite sensory nerve fibres through the TRP channel ANKTM1," *Nature* 427:260-265, Nature Publishing Group (2004).

Keown, W., et al., "Methods for Introducing DNA into Mammalian Cells," *Meth. Enzymol.* 185:525-537, Academic Press, Inc. (1990).

Kinnamon, S.C., "Taste transduction: a diversity of mechanisms," *Trends Neurosci.* 11:491-496, Elsevier Publications Cambridge (1988).

Liang, R., et al., "Parallel Synthesis and Screening of a Solid Phase Carbohydrate Library," *Science* 274:1520-1522, American Association for the Advancement of Science (1996).

Mansour, S.L., et al., "Disruption of the proto-oncogene *int-2* in mouse embryo-derived stem cells: a general strategy for targeting mutations to non-selectable genes," *Nature* 336:348-352, Macmillan Magazines Ltd. (1988).

Margolskee, R.F., "Molecular Mechanisms of Bitter and Sweet Taste Transduction," *J. Biol. Chem.* 277:1-4, The American Society for Biochemistry and Molecular Biology (2002).

Misteli, T., and Spector, D.L., "Applications of the green fluorescent protein in cell biology and biotechnology," *Nat. Biotechnol.* 15:961-963, Nature America, Inc., (1997).

Morris, K.V., "Therapeutic potential of siRNA-mediated transcriptional gene silencing," *BioTechniques* 40:7-13, The International Journal of Life Sciences Methods (Apr. 2006).

Neher, E., and Sakmann, B., et al., "The Patch Clamp Technique," *Sci. Amer.* 266:44-51, John McGrail (1992).

Park, K.-S., et al., "Phenotypic alteration of eukaryotic cells using randomized libraries of artificial transcription factors," *Nat. Biotechnol.* 21:1208-1214, Nature Publishing Group (2003).

Story, G.M., et al., "ANKTM1, a TRP-like Channel Expressed in Nociceptive Neurons, Is Activated by Cold Temperatures," *Cell* 112:819-829, Cell Press (2003).

Vaughan, T.J., et al., "Human Antibodies with Sub-nanomolar Affinities Isolated from a Large Non-immunized Phage Display Library," *Nat. Biotechnol.* 14:309-314, Nature Publishing Company (1996).

Wu, C.-F., et al., "Dissociated Neurons from Normal and Mutant *Drosophila* Larval Central Nervous System in Cell Culture," *J. Neurosci.* 3:1888-1899, Society for Neuroscience (1983).

Zochowski, M., et al., "Imaging Membrane Potential with Voltage-Sensitive Dyes," *Bio. Bull.* 198:1-21, The Marine Biological Laboratory (2000).

Xu, H., et al., "Camphor Activates and Strongly Desensitizes the Transient Receptor Potential Vanilloid Subtype 1 Channel in a Vanilloid-Independent Mechanism," *J. Neurosci.* 25:8924-8937, Society for Neuroscience (Sep. 2005).

Clapham, D.E., et al., "International Union of Pharmacology, XLIX. Nomenclature and Structure-Function Relationships of Transient Receptor Potential Channels," *Pharmacological Reviews* 57:427-450, The American Society for Pharmaceutical and Experimental Therapeutics (2005).

Hjerling-Leffler, J., et al., "Emergence of Functional Sensory Subtypes as Defined by Transient Receptor Potential Channel Expression," *The Journal of Neuroscience* 27:2435-2443, Society for Neuroscience (Mar. 2007).

\* cited by examiner

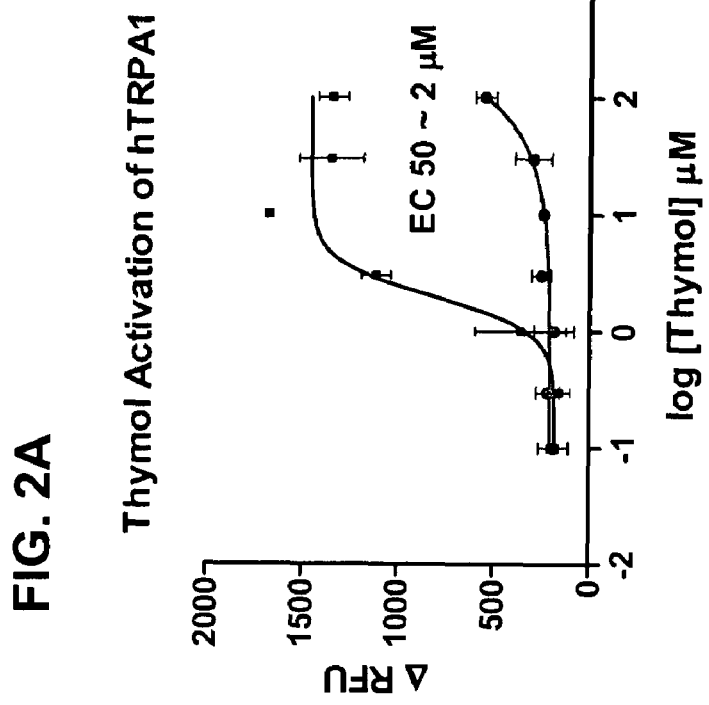
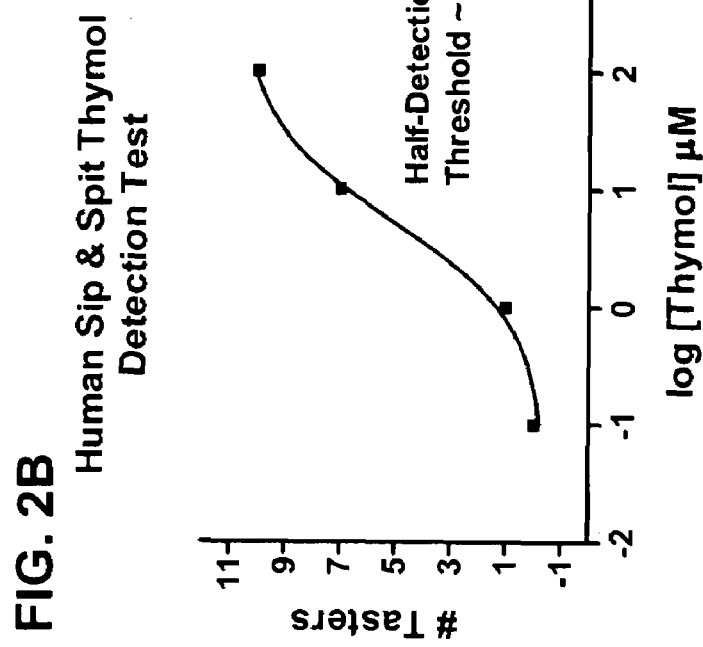
FIG. 2B
FIG. 2A

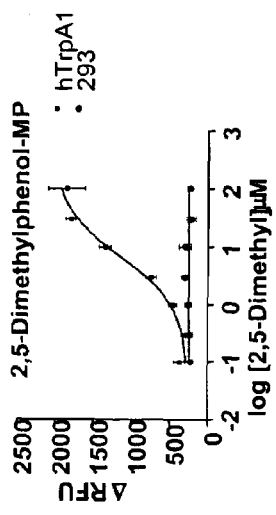
FIG. 4A
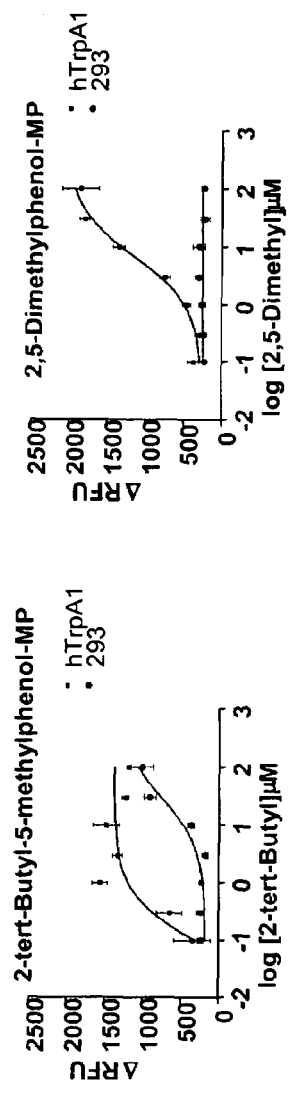
FIG. 4B
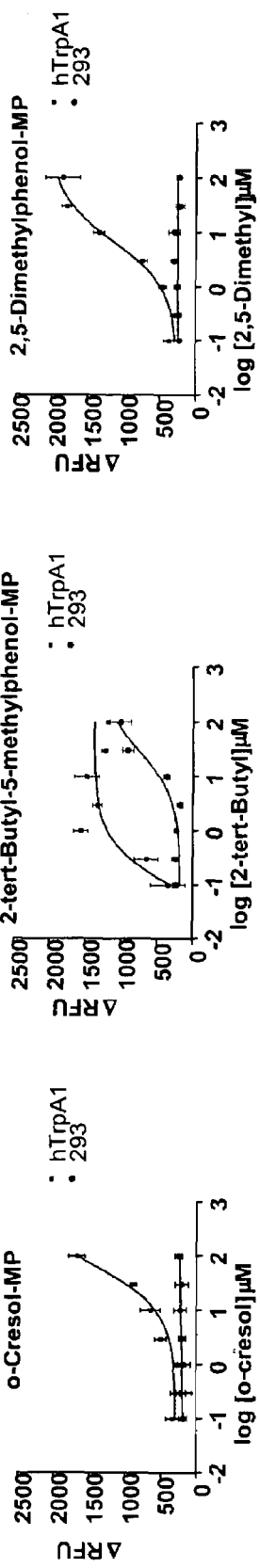
FIG. 4C
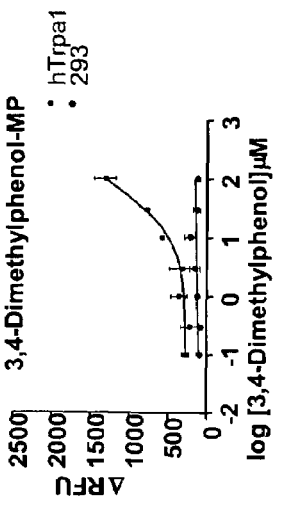
FIG. 4D
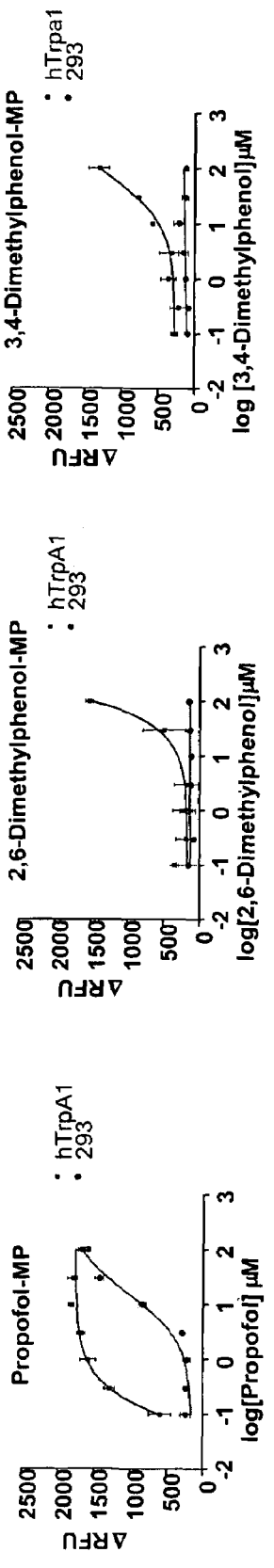
FIG. 4E
FIG. 4F

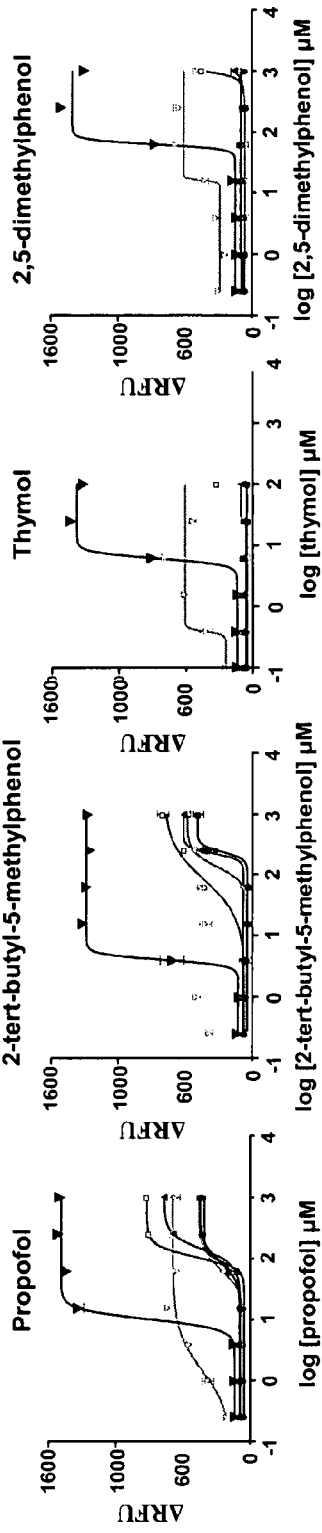
FIG. 6A Propofol
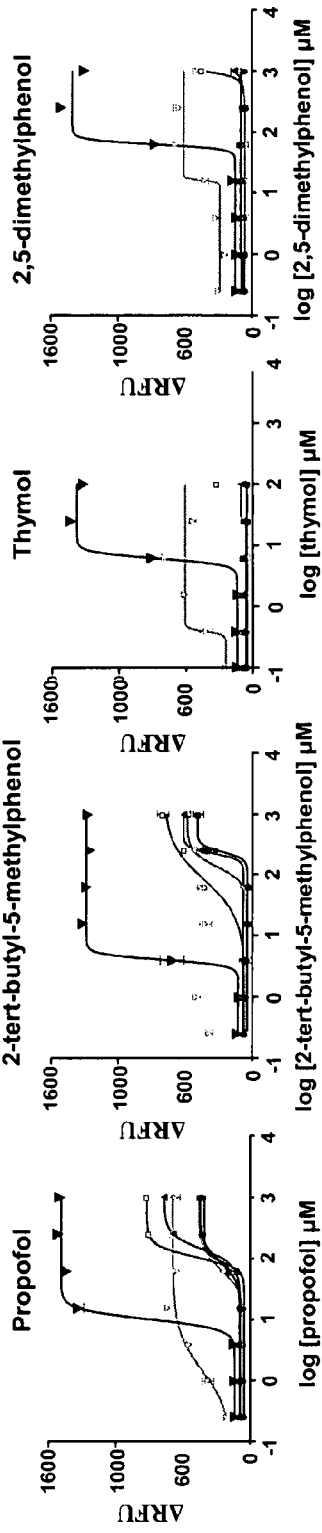
FIG. 6B 2-tert-butyl-5-methylphenol
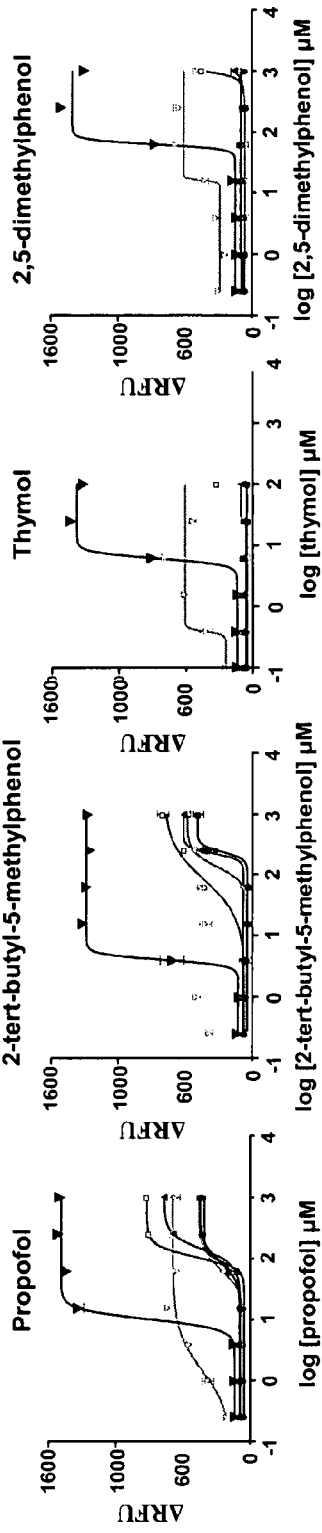
FIG. 6C Thymol
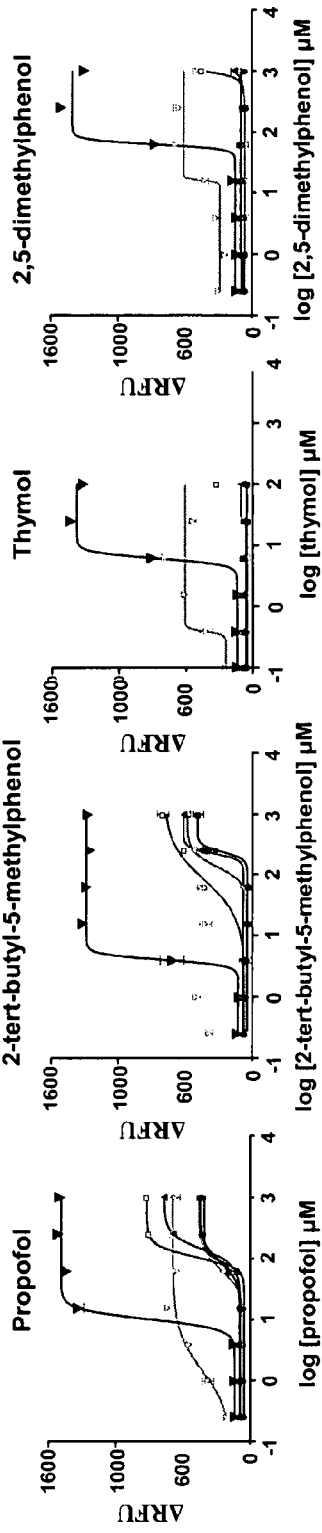
FIG. 6D 2,5-dimethylphenol
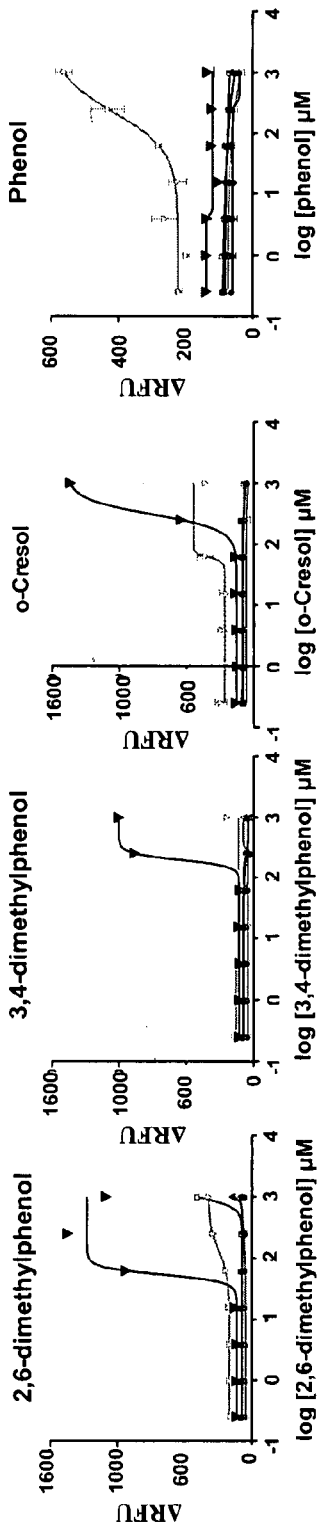
FIG. 6E 2,6-dimethylphenol
FIG. 6F 3,4-dimethylphenol
FIG. 6G o-Cresol
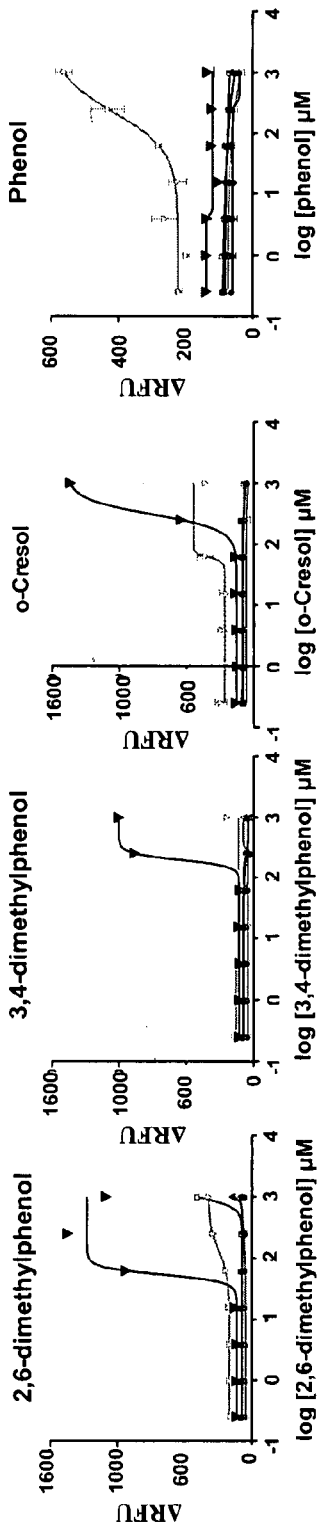
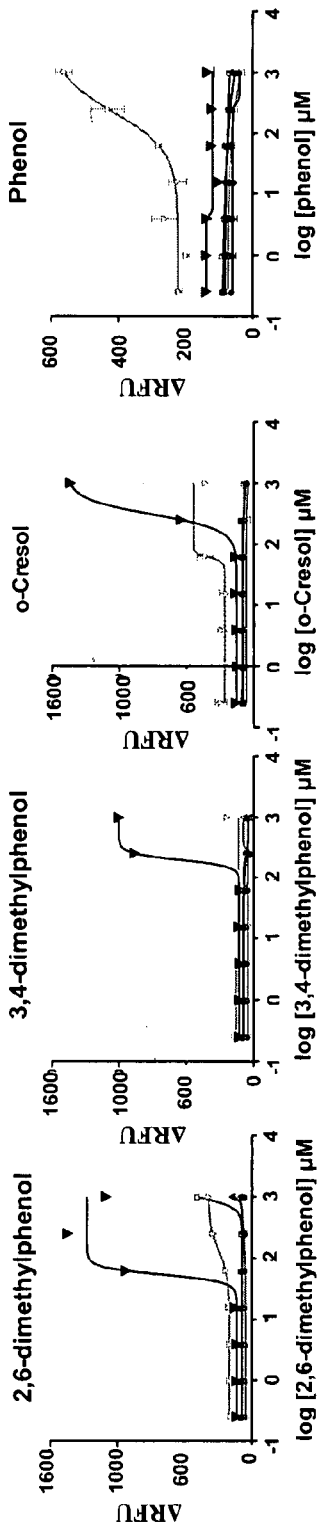
FIG. 6H Phenol
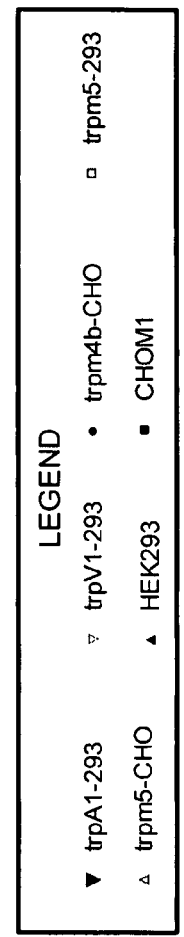
LEGEND
▼ trpA1-293  ▽ trpV1-293  ● trpm4b-CHO  □ trpm5-293
△ trpm5-CHO  ▲ HEK293  ■ CHOM1

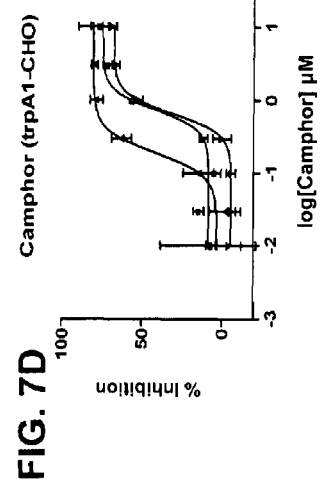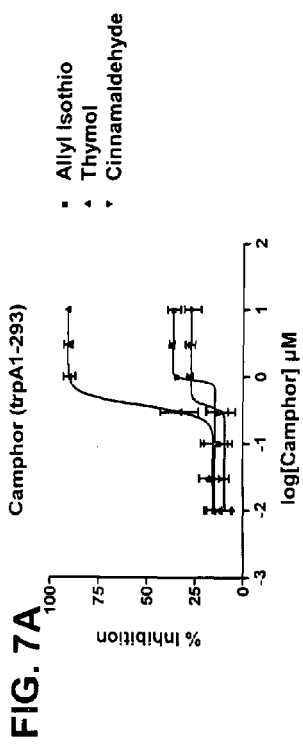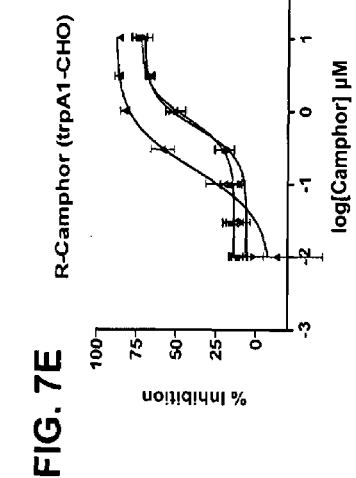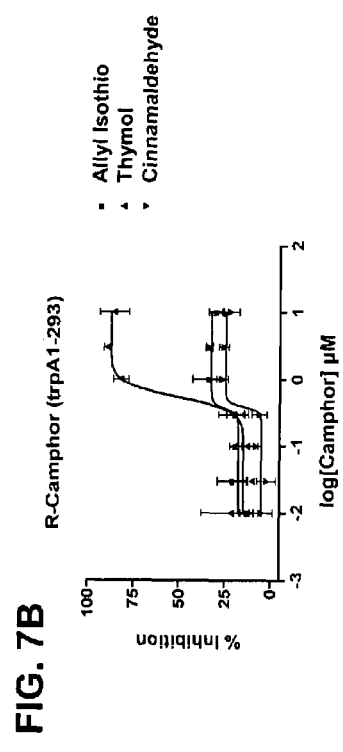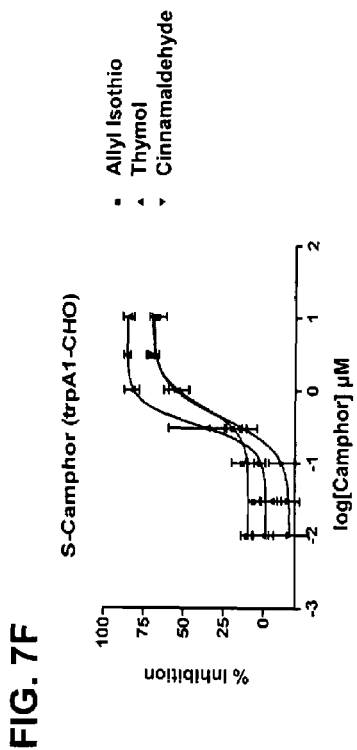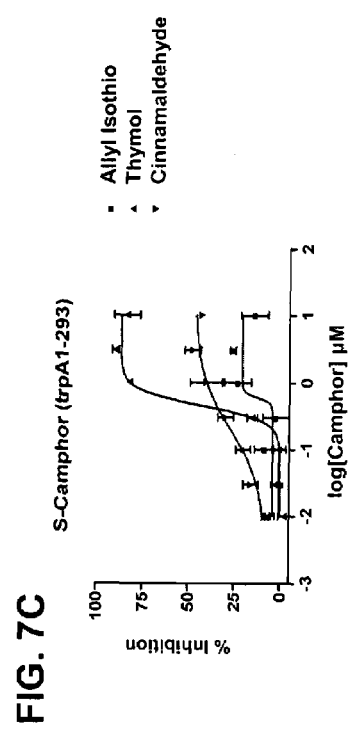
FIG. 7A   FIG. 7D
FIG. 7B   FIG. 7E
FIG. 7C   FIG. 7F

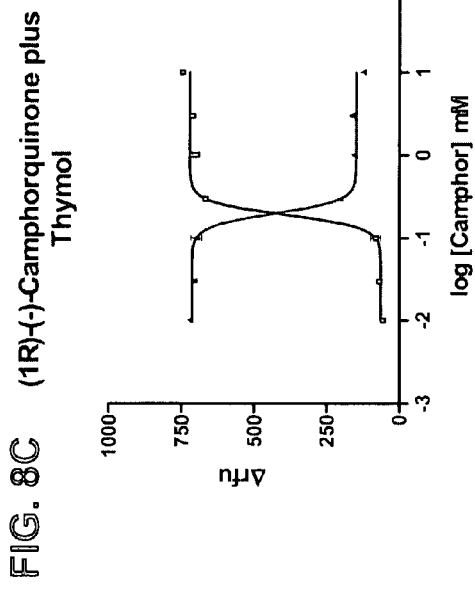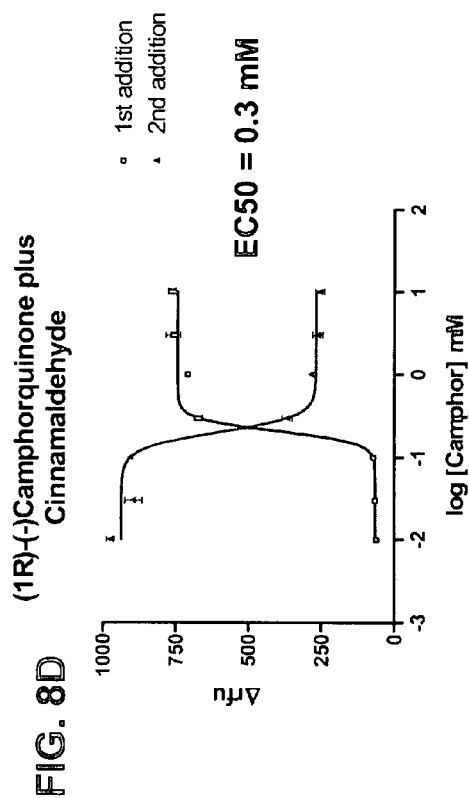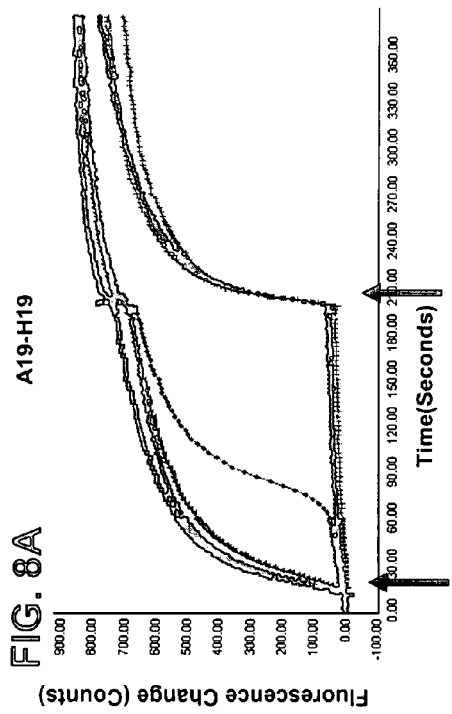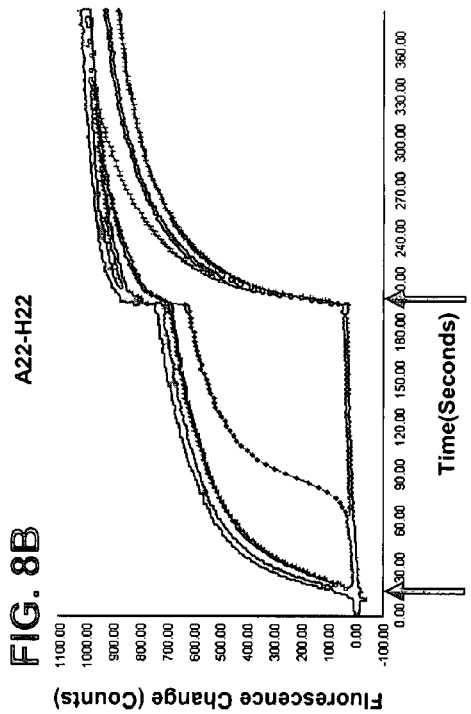

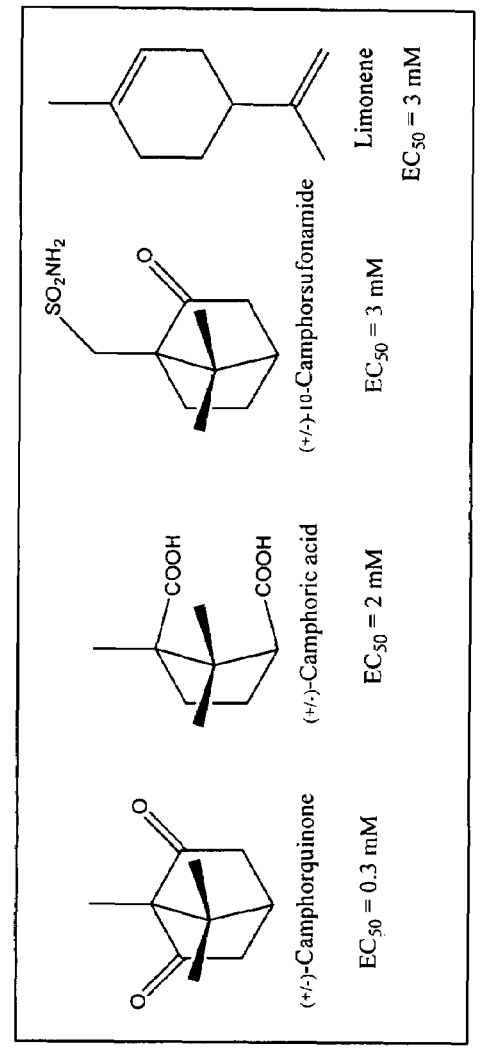
FIG. 11B Not Active as Thymol Antagonists but Have Agonist Activity
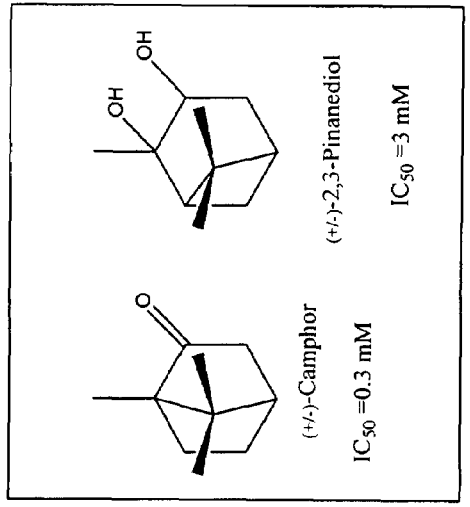
FIG. 11A Thymol Antagonists at TRPA1

| Compound | EC$_{50}$ mM (95% CI) |
|---|---|
| 2,6-isopropylphenol | 0.194 (85-440) |
| Thymol | 2 (0.5-4) |
| 2,5-dimethylphenol | 2 (1-3) |
| O-Cresol | 5 (3-8) |
| Phenol | 35 (15-84) |

SCREENING ASSAY FOR INHIBITORS OF TRPA1 ACTIVATION BY A LOWER ALKYL PHENOL

CROSS REFERENCE TO RELATED APPLICATIONS

This application claims the benefit of U.S. Prov. Appl. No. 60/833,481, filed on Jul. 27, 2006.

BACKGROUND OF THE INVENTION

1. Field of the Invention

The present invention is related to a screening method to identify compounds that impact taste. More specifically, the present invention relates to a screening method useful in the identification of compounds that affect taste sensation by modulating the level of activation of the ion channel TRPA1. The screening method allows for the rapid screening of candidate compounds by providing a visual fluorescent readout that can be easily automated.

2. Background

Taste perception plays a critical role in the nutritional status and survival of both lower and higher animals (Margolskee, R. F. *J. Biol. Chem.* 277:1-4 (2002); Avenet, P. and Lindemann, B. *J. Membrane Biol.* 112:1-8 (1989)). The ability to taste has significance beyond providing people with pleasurable culinary experiences. For example, the ability to taste allows us to identify tainted or spoiled foods, and provides satisfying responses that may be proportionate to caloric or nutritive value.

Although taste perception is a vital function, sometimes it is useful to modify certain tastes. For example, many active ingredients in medicines produce undesirable tastes, such as a bitter taste or a pungent burning sensation. Inhibition of this bitter taste or burning sensation could lead to improved acceptance by the patient. In other circumstances, it may be desirable to enhance the unpleasant taste of something that would be toxic if ingested. For instance, an increased bitterness or burning quality could prevent consumption of poisonous materials that ordinarily have little or no taste. For example, denatonium benzoate, a highly bitter compound is added to methanol and other poisonous liquids to discourage their ingestion.

Thymol, an antibacterial that is the active ingredient in, for example, mouthwash, toothpaste and lip balms, has an unpleasant taste. It is responsible for the pungent burning sensation associated with mouthwash and toothpaste, which limits patient acceptance of these products. Other compounds similar to thymol can also produce an unpleasant taste sensation.

The inclusion of compounds that could inhibit, or at least modulate, the unpleasant taste sensation of ingredients like thymol, could improve patient compliance with regimens using medicines or personal hygiene products containing these kinds of active ingredients. Moreover, the inclusion of compounds that could increase aversive tastes of toxic agents that normally have little taste could improve the safety of these products. Therefore, there exists a need in the art for methods that can be used to identify compounds that can modify taste perception in such ways, particularly for compounds such as thymol and similar compounds.

BRIEF SUMMARY OF THE INVENTION

The invention provides a method for screening candidate compounds to identify those that could be used to modify taste perception of thymol and other lower alkyl phenols. More specifically, the invention provides a new method for identifying a compound that modulates the level of activation of a TRPA1 ion channel that is activated by a lower alkyl phenol compound. TRPA1 is an ion channel that is a part of the taste-perception machinery. As such, modulating TRPA1 activation will affect an animal's ability to sense particular taste sensations.

An embodiment of the present invention is an assay for screening potential modulators of lower alkyl phenol activation of a TRPA1 ion channel.

A further embodiment of the present invention is an assay for screening potential modulators of thymol activation of a TRPA1 ion channel.

In some embodiments, the claimed method comprises screening for a compound that inhibits lower alkyl phenol activation of a TRPA1 ion channel. In other embodiments, the claimed method comprises screening for a compound that enhances lower alkyl phenol activation of a TRPA1 ion channel. In certain embodiments, the lower alkyl phenol is thymol.

Certain embodiments of the invention employ voltage-sensitive fluorescent dyes. Essentially any voltage-sensitive fluorescent compound that can be loaded into cells can be used. Preferably, the compound is selected to detect small variances in voltage. These fluorescent compounds can either show a decrease or an increase in fluorescence as voltage increases.

Additional embodiments of the invention employ ion-sensitive fluorescent dyes. Essentially any ion-sensitive fluorescent compound that can be loaded into cells can be used. Preferably, the compound is selected to detect low concentrations of ions. These fluorescent compounds can either show a decrease or an increase in fluorescence in the presence of certain ions.

If cells are grown on a solid support having one or multiple compartments, the fluorescence signal of the assay can be measured or detected in one or more compartments at the same time. Accordingly, a candidate modulator compound can be added to one or more compartments at a time. In additional embodiments of the claimed invention, the optical detector is selected from the group consisting of: Fluorescent Imaging Plate Reader (FLIPR®), FLEXStation, Voltage/Ion Probe Reader (VIPR), fluorescent microscope and charge-coupled device (CCD) camera, a flow cytometer, a fluorimeter, and Pathway HT.

BRIEF DESCRIPTION OF THE DRAWINGS/FIGURES

The accompanying figures, which are incorporated herein and form a part of the specification, illustrate one or more embodiments of the present invention and, together with the description, further serve to explain the principles of the invention and to enable a person skilled in the pertinent art to make and use the invention.

Figure 1B:
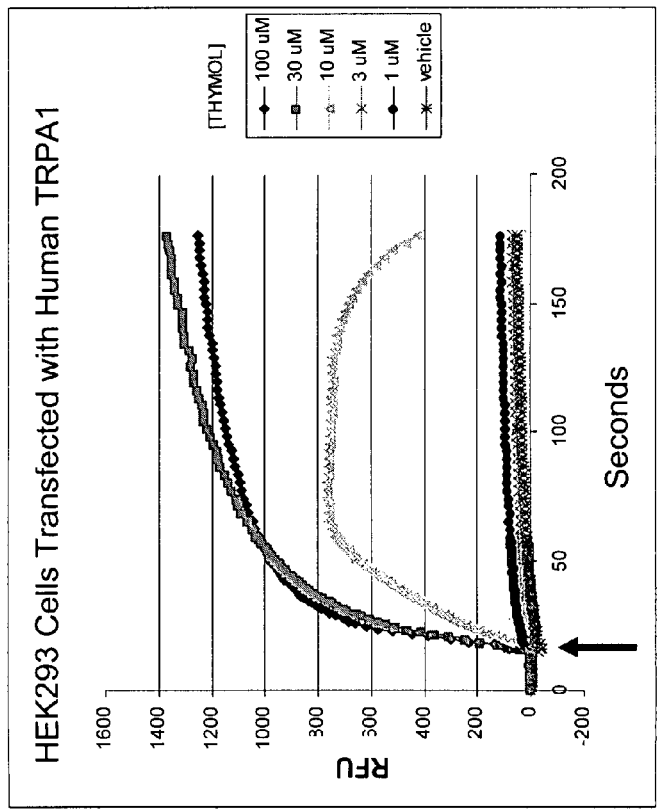

FIGS. 1A and B show fluorescent response traces upon addition of thymol (arrow) to HEK 293 cells which had been prelabeled with membrane potential dye transfected with human TRPA1 ion channels (FIG. 1A) or to non-transfected, naïve HEK 293 cells (FIG. 1B). Concentrations of thymol are shown in the legends. The results indicate that in TRPA1 expressing HEK293 cells (FIG. 1A), thymol activation triggered an influx of sodium ions into the cell. The resulting depolarization of the cell increased the fluorescent signal of the dye which was measured on the Fluorescent Imaging Plate Reader (FLIPR®). In contrast, parental HEK cells (FIG. 1B) do not respond to thymol.

FIGS. 2A and B show that the potency for thymol activation of TRPA1 is similar to median human detection threshold. FIG. 2A provides dose response curves for activation of hTRPA1 upon the addition of thymol and shows that the effective dose of 50% ($EC_{50}$) activation of TRPA1 by thymol is about 2 μM. This in vitro value agrees well with a human sensory panel (FIG. 2B), where the average detection threshold for thymol detection in water was approximately 5 μM, and suggests that TRPA1 is the major "receptor" triggering the aversive taste of thymol in humans.

Figure 3A:
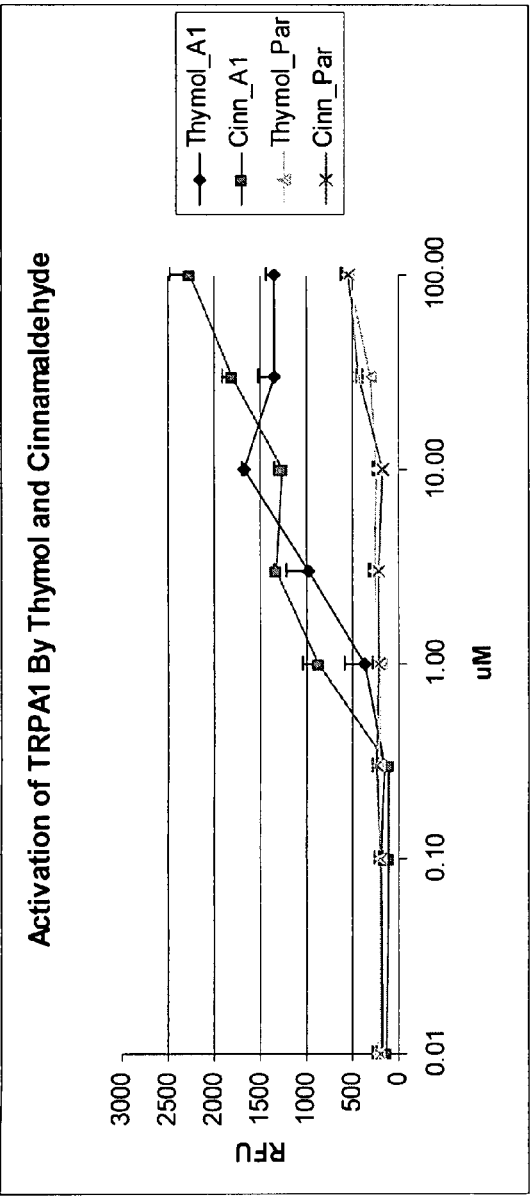
Figure 3B:
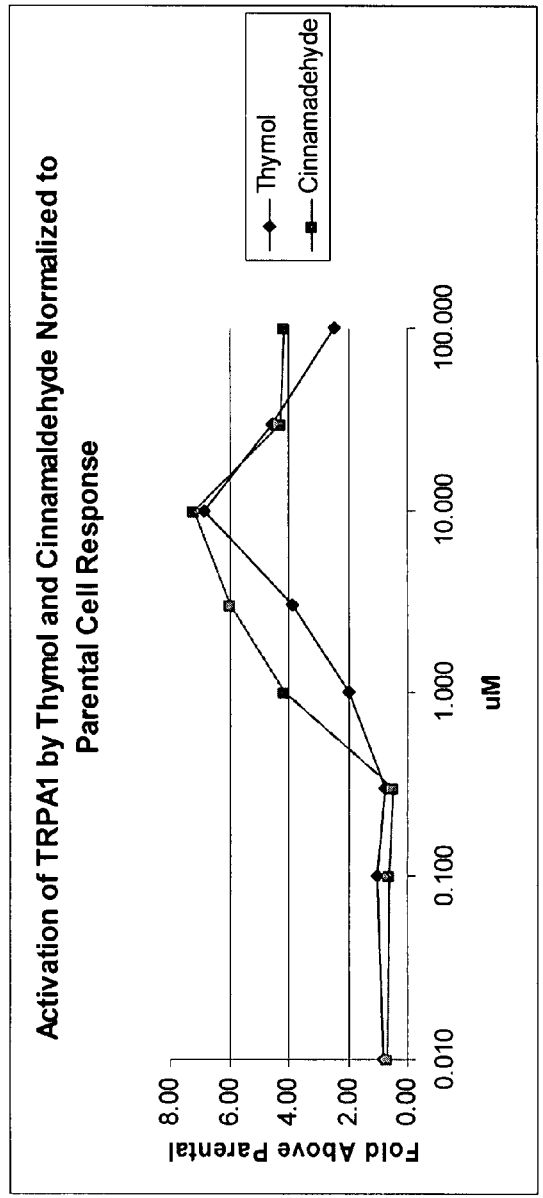

FIGS. 3A and 3B show that thymol induces TRPA1 activation at a level similar to that achieved with the known activator of TRPA1, cinnamaldehyde.

FIGS. 4A-4F shows the change in fluorescence of the membrane potential sensitive dye in HEK 293 cells in the presence of the following lower alkyl phenol compounds: o-Cresol-MP, (FIG. 4A) 2,5-Dimethylphenol-MP (FIG. 4B), 2,6-Dimethylphenol-MP (FIG. 4C), 3,4-Dimethylphenol-MP (FIG. 4D), 2-tert-Butyl-5-methylphenol-MP (FIG. 4E) and Propofol-MP (FIG. 4F). Data was collected for both HEK293 cells stably transfected with hTRPA1, and for parental HEK293 cells. The data provides a quantitative measure of TRPA1 ion channel activation and demonstrates that an increase in fluorescence in response to the presence of the lower alkyl phenol compounds occurred only in cells expressing hTRPA1. Structures of the lower alkyl phenol compounds and $EC_{50}$ values are shown in Table 1.

Figure 5A:
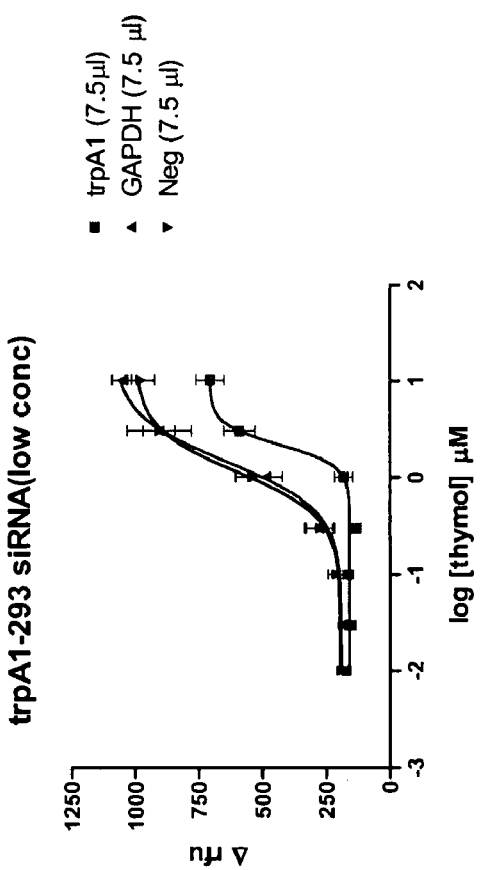
Figure 5B:
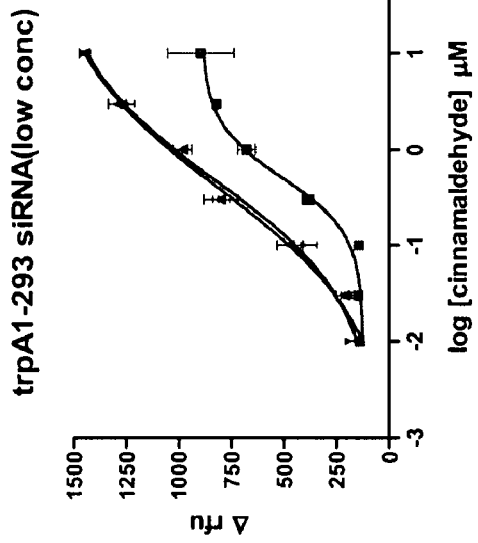

FIGS. 5A and 5B show results from an experiment evaluating thymol response in hTRPA1 expressing HEK293 cells. These results demonstrate that activation was specific for TRPA1. The specificity was determined by partial small interfering RNA (siRNA) inhibition of TRPA1 gene expression. HEK293 cells stably expressing hTRPA1 were co-transfected with one of siRNA designed for hTRPA1, GAPDH (control protein), or a negative control siRNA sequence and loaded with membrane potential sensitive dye. The cells were assayed for levels of activation in the presence of either cinnamaldehyde or thymol. Cells transfected with hTRPA1 and siRNA molecules specific for TRPA1 provided a lower increase in fluorescence upon addition of cinnamaldehyde (FIG. 5B), an established TRPA1 agonist, or thymol (FIG. 5A), than seen in cells co-transfected with hTRPA1 and one of GAPDH or saline upon addition of cinnamaldehyde or thymol.

FIGS. 6A-6H show experimental results indicating that lower alkyl phenols selectively activate TRPA1 ion channels vs related channels. HEK 293 cells expressing hTRPA1, TRPV1 or TRPM5, and CHO cells expressing TRPM4b or TRPM5 were subjected to the assay described herein in the presence of increasing concentrations of phenol and lower alkyl phenol compounds. FIG. 6 shows an increase in fluorescence of HEK 293 cells expressing TRPA1 in the presence of lower alkyl phenol compounds (FIGS. 6A-6G), but not in the presence of phenol (FIG. 6H). FIG. 6H also shows an increase in fluorescence of HEK 293 cells expressing TRPV1 in the presence of phenol, but no increase in cells expressing TRPA1, TRPM5, or TRPM4b in the presence of phenol.

FIGS. 7A-7F show results from an experiment evaluating selective inhibition of thymol activated TRPA1 by camphor. HEK293 and CHO cells expressing hTRPA1 were loaded with membrane sensitive fluorescent dye and stimulated with thymol. Camphor, including the R and S forms of camphor, fully inhibited thymol activated TRPA1 expressed in HEK293 cells with an $IC_{50}$ of 0.3 mM (FIGS. 7A-C). Camphor, including the R and S forms of camphor, fully inhibits thymol, and potentially inhibits allyl isothiocyanate, and cinnamaldehyde activated TRPA1 expressed in CHO cells (FIGS. 7D-F). Each of thymol, allyl isothiocyanate, and cinnamaldehyde activated TRPA1 expressed in HEK293 cells is fully inhibited by camphors although thymol activation is more sensitive to camphor inhibition.

FIGS. 8A and 8B provides fluorescent traces of HEK 293 cells treated with camphorquinone (first arrow) and then the TRPA1 agonist thymol (FIG. 8A) or cinnamaldehyde (FIG. 8B) (second arrow). Response curves show camphorquinone inhibition via desensitization of thymol (FIG. 8C) or cinnamaldehyde (FIG. 8D) responses. FIGS. 8C and 8D indicate that a close analog of camphor, camphorquinone, triggers an agonist response in TRPA1 with an $EC_{50}$ of about 0.3 mM. Subsequent inhibition of stimulation by thymol or cinnamaldehyde is most likely due to channel desensitization.

Figure 9:
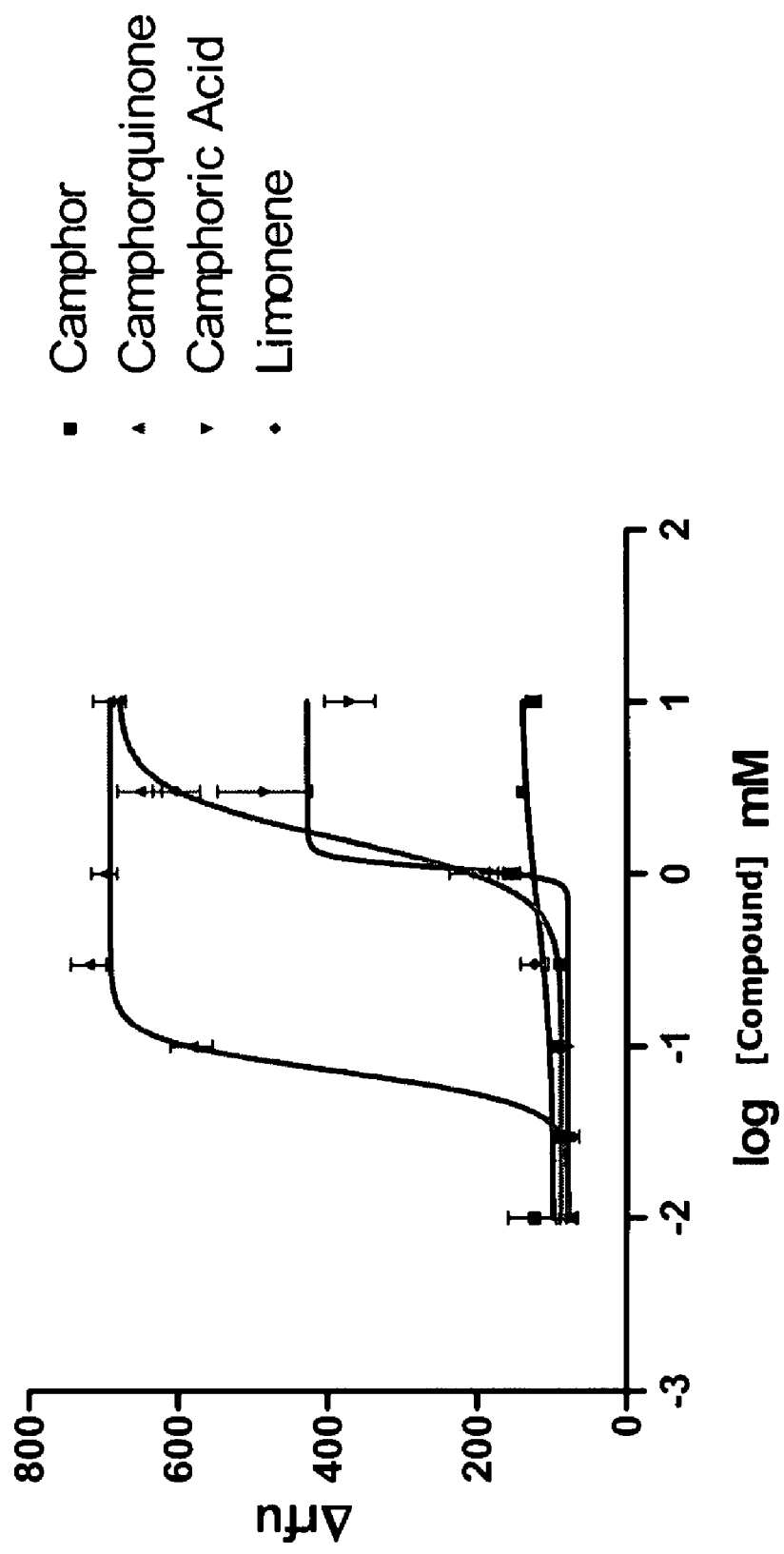

FIG. 9 shows data indicating that other related sesquiterpines, camphoric acid and limonene are TRPA1 agonists. Camphor has no agonist activity.

Figure 10:
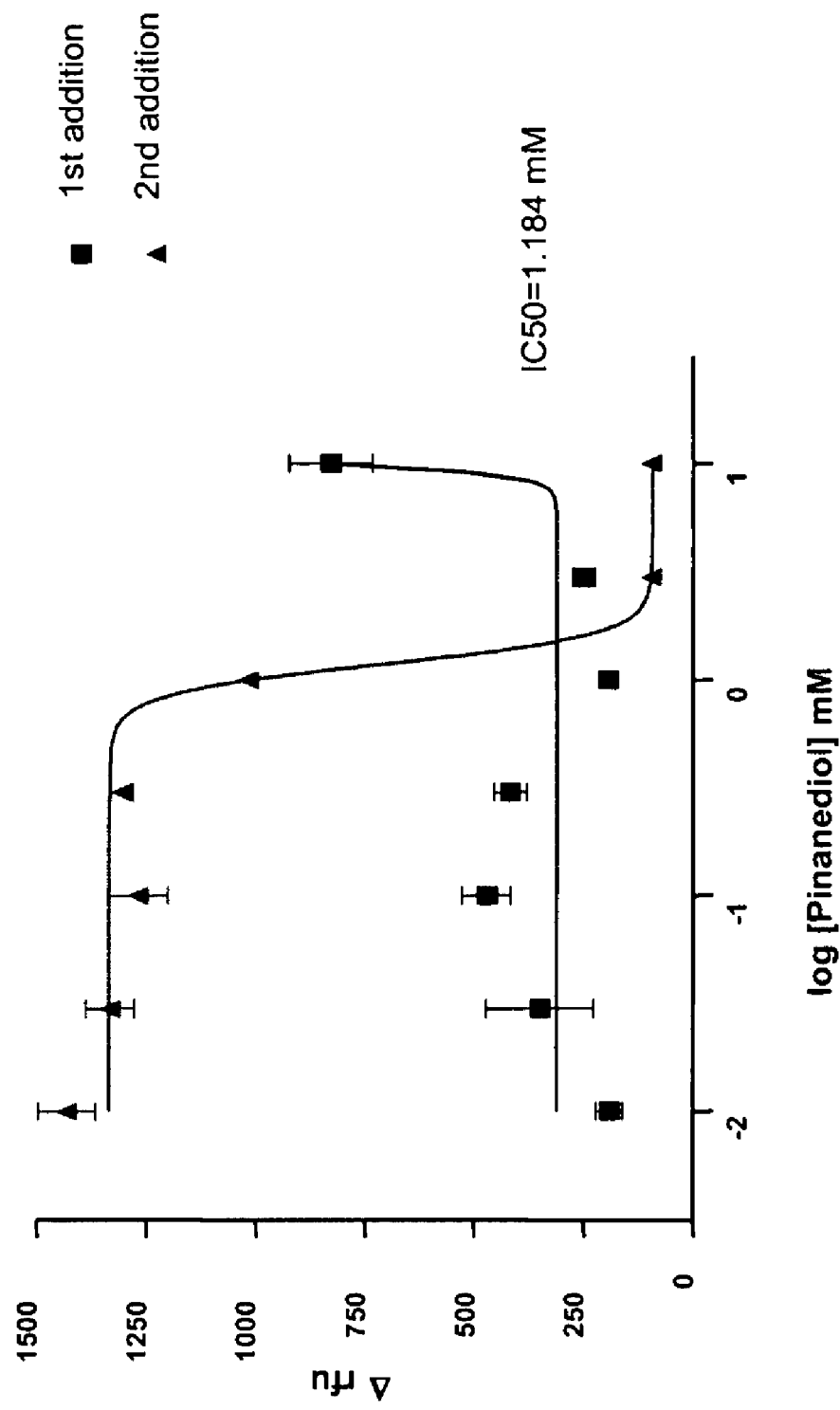

FIG. 10 demonstrates that, unexpectedly, a related sesquiterpines pinanediol exhibits an inhibitory effect, albeit weak, of thymol activation of TRPA1. Pinanediol +/− isomers were added to TRPA1 transfected HEK cells followed by addition of thymol (10 μM). Neither isomer (+ shown) had a significant agonist activity until 10 mM however both inhibited TRPA1 activation at 1 mM.

FIGS. 11A and 11B show structures and agonist and antagonist activation by thymol around the camphor backbone.

Figures 12A, 12B, 12C, 12D, 12E, 12F:
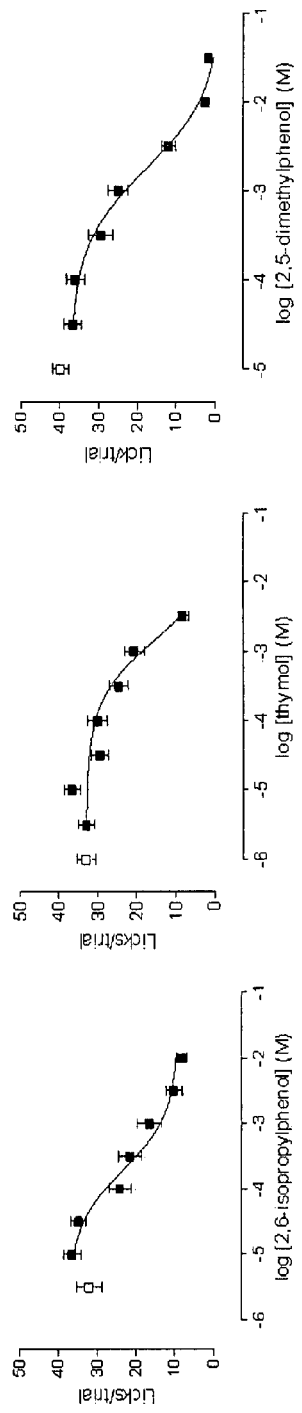

FIGS. 12A-12F show experimental results indicating that increasing concentrations of lower alkyl phenols cause taste aversion in mice. Mice were subjected to the assay described in Example 6 in the presence of increasing concentrations of phenol and other lower alkyl phenol compounds. The number of times that a given animal licked solutions of lower alkyl phenol compounds was recorded. FIG. 12A-12E show a decrease in licks/trial in mice exposed to increasing concentrations of 2,6-isopropylphenol, thymol, 2,5-dimethylphenol, o-cresol and phenol, respectively. FIG. 12F shows the $EC_{50}$ values of phenol and other lower alkyl phenol compounds as measured in mM.

DETAILED DESCRIPTION OF THE INVENTION

The screening assay described and claimed herein allows for screening of compounds to identify a compound that modulates the level of activation of a TRPA1 ion channel that has been activated by a lower alkyl phenol compound, e.g., thymol. The assay enables candidate compounds be screened to determine whether they modulate lower alkyl phenol activation of a TRPA1 ion channel, and thus, taste perception.

Taste is the ability to respond to dissolved molecules and ions called tastants. Humans detect taste with taste receptor cells (TRCs), which are clustered in taste buds. (Kinnamon, S. C. *TINS* 11:491-496 (1988)). Tastants bind specific receptors on the TRC's cell membrane, leading to a voltage change across the cell membrane. A change in voltage across the TRC cell membrane depolarizes, or changes the electric potential of the cell. This leads to a signal being sent to a sensory neuron leading back to the brain.

Ion channels are transmembrane proteins that form pores in a cell membrane and allow ions to pass from one side to the other (reviewed in B. Hille (Ed), 1992, Ionic Channels of Excitable Membranes 2nd ed., Sinauer, Sunderland, Mass.). Many channels have "gates" that open in response to a specific stimulus. As examples, voltage-gated channels respond to a change in the electric potential across the membrane, mechanically-gated channels respond to mechanical stimulation of the membrane, and ligand-gated channels respond to the binding of specific molecules. Various ligand-gated channels can open in response to extracellular factors, such as a neurotransmitters (transmitter-gated channels), or intracellular factors, such as ions (ion-gated channels), or nucleotides (nucleotide-gated channels). Still other ion channels are modulated by interactions with other proteins, such as G-proteins (G-protein coupled receptors or GPCRs).

Most ion channels mediate the permeation of one predominant ionic species. For example, sodium ($Na^+$), potassium ($K^+$), chloride ($Cl^-$), and calcium ($Ca^{2+}$) channels have been identified.

The transient receptor potential (TRP) family ion channels have been implicated in the mechanisms controlling several relevant physiological responses, including temperature and mechanical stimulation, responses to painful stimuli, taste, and pheromones. (Calixto, J. B. et al., *Pharmacology and Therapeutics* 106:179-208 (2005)). The TRP family of ion channels has been subdivided into four main classes: TRPC (short cannonical TRP channels); TRPM (long, TRP melastatin channels); TRPV (vanilloid receptor TRP channels); and TRPA (short ankyrin-repeat TRP channels). (Clapham, D. E. et al., *Pharmacol. Rev.* 55:591-596 (2003)). One member of the TRP family, TRPA1, has been shown to be sensitive to low temperatures, with activation of the channel occurring at an average temperature of about 18° C. (about 64° F.). (Story, G. M. et al., *Cell* 112: 819-829 (2003)).

TRPA1 channels are also activated by naturally occurring substances such as isothiocyanate compounds, $\Delta^9$-tetrahydrocannabinol (THC), and cinnamaldehyde. (Jordt, S. E. et al., *Nature* 427: 260-265 (2004); Bandell, M. et al., *Neuron* 41: 849-857 (2004)). In addition, mouse TRPA1-CHO cells show a sharp increase in intracellular free $Ca^{2+}$ upon application of several plant derived compounds such as eugenol (from clove oil), gingerol (from ginger) and methyl salicylate (from wintergreen oil). (Blandell. M. et al.) Allyl isothiocyanate, cinnamaldehyde, eugenol, gingerol and methyl salicylate cause a pungent burning sensation in humans. Cinnamaldehyde is a key component responsible for cinnamon flavor.

Eugenol, gingerol and methyl salicylate have been shown to activate TRPV1 and TRPM8 in addition to TRPA1 and thus, produce their pungent activity through the stimulation of a variety of TRP ion channels. (Calixto et al.). In contrast, allyl isothiocyanate and cinnemaldehyde are specific activators of TRPA1. TRPA1 may be responsible for the burning taste sensory quality of allyl isothiocyanate and cinnemaldehyde. Thus, TRPA1 plays a role in taste perception.

Because TRPA1 is a part of the taste-perception machinery, modulation of TRPA1 activity can affect an animal's ability to sense particular taste sensations. Although taste perception is a vital function, the inhibition, or masking, of undesirable tastes would be beneficial under certain circumstances. For example, many active pharmaceutical ingredients of medicines produce undesirable tastes, such as a bitter taste, or a pungent burning sensation. Inhibition of the bitter taste or burning sensation produced by the active pharmaceutical ingredient will lead to improved acceptance by the patient. In other circumstances, enhancing the unpleasant taste or the ability to produce a burning sensation of active pharmaceutical ingredients that may be harmful if ingested is also be desirable. For instance, an increased bitterness or burning quality can prevent consumption of poisonous materials that ordinarily have little or no taste, or sensation associated with them.

Thymol is an antibacterial and is the active ingredient in, for example, mouthwash, toothpaste and lip balms. However, thymol is responsible for the pungent burning sensation associated with mouthwash and toothpaste, which limits patient acceptance.

The mechanism by which thymol produces such a taste sensation had not been identified. We have surprisingly discovered that lower alkyl phenols, including thymol, specifically activate TRPA1. Thus, thymol's burning taste sensation is sensed through activation of the TRPA1 ion channel by thymol. In addition, a taste sensation produced by other lower alkyl phenols is sensed through activation of the TRPA1 ion channel.

Thus, a compound that modulates lower alkyl phenol activation of TRPA1 would affect the taste sensation produced by lower alkyl phenols, including the burning taste sensation produced by thymol. For example, a compound that inhibits thymol activation of TRPA1 could reduce or block the burning taste sensation produced by thymol, and lead to greater patient acceptance of products containing it.

The invention provides a method for screening a candidate compound to identify a compound that modulates activation of TRPA1 by Compound I, wherein Compound I is represented by Formula I:

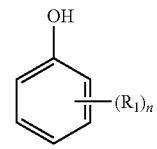

wherein each instance of $R_1$ is independently hydrogen or a $C_{1-6}$ alkyl, and n is an integer from 1-5, said method comprising:
(i) measuring the level of activation of Compound I-activated-TRPA1 in the presence of a candidate compound to obtain a measured value; and
(ii) comparing said measured value to a standard value, wherein a difference between the measured value and the standard value indicates that the candidate compound modulates Compound I activation of TRPA1.

In addition, the assay provides a method for identifying a compound that modulates the activation of TRPA1 by Compound I, comprising:
(a) incubating cells expressing TRPA1 with an indicator for a time sufficient to allow incorporation of the indicator into the cells, wherein the indicator is capable of signaling activation of TRPA1;
(b) incubating said cells with a candidate compound while maintaining said cells in a solution that contains Compound I and is suitable to allow a flux of ions through TRPA1;
(c) after completing steps (a) and (b), measuring a signal from the indicator in the presence of the candidate modulator compound; and
(d) comparing the signal of step (c) to a standard value, wherein the indicator indicates the flux of ions via Compound I-activated TRPA1 and a difference between the signal of step (c) and the standard value indicates that the candidate compound modulates TRPA1 activation.

The assay also provides a method for screening a candidate compound to identify a compound that modulates activation of TRPA1 by thymol, said method comprising:
(i) measuring the level of activation of thymol-activated-TRPA1 in the presence of a candidate compound to obtain a measured value; and (ii) comparing said measured value to a standard value, wherein a difference between the measured value and the standard value indicates that the candidate compound modulates thymol-activation of TRPA1.

In addition, the assay provides method for identifying a compound that modulates the activation of TRPA1 by thymol, said method comprising:
(a) incubating cells expressing TRPA1 with an indicator for a time sufficient to allow incorporation of the indicator into the cells, wherein the indicator is capable of signaling activation of TRPA1;
(b) incubating said cells with a candidate compound while maintaining said cells in a solution that contains thymol and is suitable to allow a flux of ions through TRPA1;
(c) after completing steps (a) and (b), measuring a signal from the indicator in the presence of the candidate modulator compound; and
(d) comparing the signal of step (c) to a standard value, wherein the indicator indicates the flux of ions via thymol-activated TRPA1 and a difference between the signal of step (c) and the standard value indicates that the candidate compound modulates TRPA1 activation.

In the claimed assay, the cell is exposed to a candidate compound and the level of activation of the lower alkyl phenol-activated TRPA1 ion channel is measured. The level of activation of the lower alkyl phenol-activated TRPA1 ion channel in the presence of the candidate compound is compared to a standard value. The comparison indicates the ability of the candidate compound to modulate the level of activation of the lower alkyl phenol-activated TRPA1 ion channel. The assay can provide both a qualitative and a quantitative indication of ion channel activation and the modulation of that activation.

A preferred method of the invention comprises contacting a cell expressing TRPA1 with a lower alkyl phenol, wherein the cell has been preloaded with a fluorescent dye capable of providing an indication of TRPA1 ion channel activation; contacting the cell with a candidate modulating compound; measuring the fluorescent intensity of the cell in the presence of said candidate modulating compound using an optical detector; and comparing the measured fluorescent intensity to a standard value, wherein a change in the measurement of activation of lower alkyl phenol-activated TRPA1 in the presence of the candidate compound indicates that the candidate compound modulates lower alkyl phenol-activated activation of TRPA1, and provides, if necessary, a quantitative measure of modulation of the level of activation of lower alkyl phenol-activated TRPA1. In a preferred method, the lower alkyl phenol is thymol.

The quantitative measure of modulation of the level of activation of lower alkyl phenol-activated TRPA1 obtained for a candidate compound can be compared to that of a compound known to modulate the level of activation of lower alkyl phenol-activated TRPA1. Such a comparison provides an indication of the effectiveness with which the candidate compound can modulate the level of activation of lower alkyl phenol-activated TRPA1.

A means of evaluating specificity of a compound to modulate a channel can be performed in parallel with the above described method. These parallel methods include the use of small interfering RNAs (siRNAs). siRNAs are a class of 20-25 nucleotide-long RNA molecules that interfere with the expression of genes. They can be exogenously introduced to cells by investigators to bring about the knockdown or suppression of expression of a particular gene. By introducing siRNAs into a cell transfected with a plasmid containing the gene for a TRP channel, expression of the TRP channel can be suppressed. This experiment allows investigators to evaluate the specificity of a compound to modulate the channel being investigated.

In the claimed assay, a measured value that is above the standard value indicates that Compound 1 has activated the TRPA1 ion channel. That the TRPA1 ion channel is activated upon addition of Compound I is determined upon finding a measured value that is between about 1.3 and about 10 times the standard value.

In one embodiment, the measured value obtained can be compared to a known value. A known value is the level of TRPA1 activation induced by a compound known to activate TRPA1, e.g., cinnemaldehyde. When comparing a measured value to a known value, a measured value that is at least about 10% of the known value indicates that the compound is capable of activating TRPA1.

As used in the specification and claims, the singular form "a", "an" and "the" includes plural references unless the context clearly dictates otherwise. For example, the term "an ion channel" includes a plurality of ion channels. The term "a cell" includes a plurality of cells. The term "a compound" includes a plurality of compounds.

"Alkyl" includes straight-chained and branched $C_{1-6}$ alkyl groups. Typical $C_{1-6}$ alkyl groups include methyl, ethyl, propyl, isopropyl, butyl, sec-butyl, tert-butyl and 3-pentyl groups.

"Screening" means analyzing a compound using the assay described herein. "Measuring" means to ascertain the quantity or capacity.

"Lower alkyl phenol activation of TRPA1," "lower alkyl phenol-activated TRPA1," "Compound I activation of TRPA1," and "Compound I-activated TRPA1" refer to TRPA1 ion channels that are activated by the presence of a lower alkyl phenol. The activation can be initiating TRPA1 activity by the presence of a lower alkyl phenol, increasing TRPA1 activity by the presence of a lower alkyl phenol or both.

"Thymol activation of TRPA1" and "thymol-activated TRPA1" refer to TRPA1 ion channels that are activated by the presence of thymol. The activation can be initiating TRPA1 activity by the presence of thymol, increasing TRPA1 activity by the presence of thymol, or both.

Active TRPA1 permits or facilitates ion flux across a cell membrane. "TRPA1 activity" is the capacity of TRPA1 to permit or facilitate ion flux across a cell membrane. Ion flux refers to both influx or efflux of ions.

"Standard value" refers to a negative or positive control value. The standard value provides a control value against which the measurement of activation of the lower alkyl phenol-activated TRPA1 in the presence of a candidate compound can be compared. For example, a measurement of the activation of lower alkyl phenol-activated TRPA1 in the presence of a candidate compound could be compared to a measurement of the activation of lower alkyl phenol-activated TRPA1 in the absence of the candidate compound to provide a quantitative measurement of the ability of the candidate compound to modulate the level of activation of lower alkyl phenol-activated TRPA1. Additional standard values include, for example, (1) a measurement of the level of activation of TRPA1 that has not been activated by a lower alkyl phenol in the presence of the candidate compound, or (2) a measurement of the level of activation of cells that do not express TRPA1 in the presence of a lower alkyl phenol and the candidate compound. Further standard values can be easily determined by those skilled in the art and tailored to suit the particular requirements of the experiments performed.

"Modulate" as used herein includes any alteration, directly or indirectly, of the movement of ions through an ion channel. This includes blocking or inhibiting the level of activation of the channel in the presence of, or in response to, an appropriate stimulator. Alternatively, modulators may enhance the level of activation of the channel. "Enhance" as used herein, includes any increase directly or indirectly, of the movement of ions through an ion channel. The modulating compound or agent may exert its effect by directly occluding the pore, by binding and preventing the opening of the pore, by binding and promoting opening of the pore, or by affecting the time and frequency of the opening of the ion channel.

TRPA1 Expressing Cells

The practitioner may use cells in which TRPA1 is endogenous or may introduce TRPA1 into a cell. If TRPA1 is endogenous to the cell, but the level of expression is not optimum, the practitioner may increase the level of expression of TRPA1 in the cell. Where a given cell does not produce TRPA1 at all, or at insufficient levels, a TRPA1 nucleic acid may be introduced into a host cell for expression and insertion into the cell membrane.

The introduction, which may be generally referred to without limitation as "transformation," may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. General aspects of mammalian cell host system transformations have been described in U.S. Pat. No. 4,399,216. For various techniques for transforming mammalian cells, see Keown et al., *Meth. Enzym.*, 185:527-537 (1990) and Mansour et al., *Nature* 336:348-352 (1988). As is described in detail below, TRPA1 can also be rendered non-functional. Biologically inactive TRPA1 can be introduced into cells using any of the above-described techniques. Alternatively, siRNA can be introduced into cells along with TRPA1. (Dorsett, Y. and Tuschl, T., *Nat. Rev. Drug Discov.* 3(4):318-29 (2004) and Morris, K. V., *BioTechniques* Suppl: 7-13 (2006)).

The siRNA will decrease expression of TRPA1. Cells expressing inactive TRPA1 or expressing only low quantities of active TRPA1 are useful for confirmation of the specificity of modulation of TRPA1 activation.

TRPA1 (formerly called p120, ANKTM1 or TRPN1) is a $Ca^{2+}$-permeant non-selective channel with $\approx 14$ ankyrin repeats in its amino terminus. (Janquemar, D. et al., *J. Biol. Chem.* 274:7325-7333 (1999)). The corresponding gene was identified on human chromosome 8 and encodes a protein of 1119 amino acids. Janquemar, D. et al.

The National Center for Biotechnology Information (NCBI) database lists several sequences for both the nucleic acid (NM177781) and amino acid (O75762, NP15628, NP31526, NP038658, NO808449) sequences for both the human and mouse forms of TRPA1. The inclusion of the above sequences is for the purpose of illustration of the TRPA1 genetic sequence, however the invention is not limited to one of the disclosed sequences.

It is recognized in the art that there can be significant heterogeneity in a gene sequence depending on the source of the isolated sequence. The invention contemplates the use of conservatively modified variants of TRPA1. Conservatively modified variants applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The assay described herein could also be performed using cells expression variant TRPA1 proteins. The variant TRPA1 proteins would comprise non-conservative modifications (e.g. substitutions). By "nonconservative" modification herein is meant a modification in which the wildtype residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are nonconservative modifications. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. In one embodiment, a variant TRPA1 protein could have at least one nonconservative modification. In one embodiment, a variant TRPA1 protein could result from translation of a polynucleotide in which the first 1000 base pairs of the TRPA1 gene have been deleted. In another embodiment, a variant TRPA1 protein could result from translation of a polynucleotide in which the first 2000 base pairs of the TRPA1 gene have been deleted.

Variant proteins may be generated, for example, by using a PDA™ system previously described in U.S. Pat. Nos. 6,188,965; 6,296,312; 6,403,312; alanine scanning (see U.S. Pat. No. 5,506,107), gene shuffling (WO 01/25277), site saturation mutagenesis, mean field, sequence homology, polymerase chain reaction (PCR) or other methods known to those of skill in the art that guide the selection of point or deletion mutation sites and types.

Dominant negative forms of TRPA1 may also be used in the screening assay to identify compounds that specifically modulate TRPA1. By "dominant negative" herein is meant a protein comprising at least one variant TRPA1 monomer that competes for binding to wild-type subunits such that the protein retains the ability to form an ion channel but it cannot regulate the flux of monovalent cations. Depending on the composition of the ion channel, the degree to which monovalent cation flux is inhibited will vary.

The cells used in methods of the present invention may be present in, or extracted from, organisms, may be cells or cell lines transiently or permanently transfected or transformed with the appropriate proteins or nucleic acids encoding them, or may be cells or cell lines that express the required TRPA1 from endogenous (i.e. not artificially introduced) genes.

Expression of the TRPA1 protein refers to the translation of the TRPA1 polypeptide from a TRPA1 gene sequence either from an endogenous gene or from nucleic acid introduced into a cell. The term "in situ" where used herein includes all these possibilities. Thus in situ methods may be performed in a suitably responsive cell line which expresses the TRPA1 (either as a native channel, or from a nucleic acid introduced into the cell). The cell line may be in tissue culture or may be, for example, a cell line xenograft in a non-human animal subject.

As used herein, the term "cell membrane" refers to a lipid bilayer surrounding a biological compartment, and encompasses an entire cell comprising such a membrane, or a portion of a cell.

For stable transfection of mammalian cells, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cell along with the gene of interest. Preferred selectable markers include those which confer resistance to drugs, such as G418, hygromycin and methotrexate. A nucleic acid encoding a selectable marker can be introduced into a host cell in the same vector as that encoding TRPA1, or can be introduced in a separate vector. Cells stably transfected with the introduced nucleic acid can be identified by drug selection (e.g., cells that have incorporated the selectable marker gene will survive, while the other cells die).

It should be noted that expression of TRPA1 can also be controlled by any of a number of inducible promoters known in the art, such as a tetracycline responsive element, TRE. For example, TRPA1 may be selectively presented on the cell membrane by controlled expression using the Tet-on and Tet-off expression systems provided by Clontech (Gossen, M. and Bujard, H. *Proc. Natl. Acad. Sci. USA* 89: 5547-5551 (1992)). In the Tet-on system, gene expression is activated by the addition of a tetracycline derivative doxycycline (Dox), whereas in the Tet-off system, gene expression is turned on by the withdrawal of tetracycline (Tc) or Dox. Any other inducible mammalian gene expression system may also be used. Examples include systems using heat shock factors, steroid hormones, heavy metal ions, phorbol ester and interferons to conditionally expressing genes in mammalian cells.

The cell lines used in assays of the invention may be used to achieve transient expression of TRPA1, or may be stably transfected with constructs that express a TRPA1 peptide. Means to generate stably transformed cell lines are well known in the art and such means may be used here. Examples of cells include, but are not limited to Chinese Hamster Ovary (CHO) cells, COS-7, HeLa, HEK 293, PC-12, and BAF.

The level of TRPA1 expression in a cell may be increased by introducing a TRPA1 nucleic acid into the cells or by causing or allowing expression from a heterologous nucleic acid encoding TRPA1. A cell may be used that endogenously expresses TRPA1 without the introduction of heterologous genes. Such a cell may endogenously express sufficient levels of TRPA1 for use in the methods of the invention, or may express only low levels of TRPA1 which require supplementation as described herein.

The level of TRPA1 expression in a cell may also be increased by increasing the levels of expression of the endogenous gene. Endogenous gene activation techniques are known in the art and include, but are not limited to, the use of viral promoters (WO 93/09222; WO 94/12650 and WO 95/31560) and artificial transcription factors (Park et al. *Nat. Biotech.* 21:1208-1214 (2003).

The level of TRPA1 expression in a cell may be determined by techniques known in the art, including but not limited to, nucleic acid hybridization, polymerase chain reaction, RNase protection, dot blotting, immunocytochemistry and Western blotting. Alternatively, TRPA1 expression can be measured using a reporter gene system. Such systems, which include for example red or green fluorescent protein (see, e.g. Mistili and Spector, *Nature Biotechnology* 15:961-964 (1997), allow visualization of the reporter gene using standard techniques known to those of skill in the art, for example, fluorescence microscopy. Furthermore, the ability of TRPA1 to be activated by known positive modulating compounds, such as thrombin, may be determined following manipulation of the TRPA1 expressing cells.

Cells described herein may be cultured in any conventional nutrient media. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

The cells can be grown in solution or on a solid support. The cells can be adherent or non-adherent. Solid supports include glass or plastic culture dishes, and plates having one compartment, or multiple compartments, e.g., multi-well plates.

The number of cells seeded into each well are preferably chosen so that the cells are at or near confluence, but not overgrown, when the assays are conducted, so that the signal-to-background ratio of the signal is increased.

TRPA1 Activation

To observe TRPA1 channel activation, and evaluate whether a candidate compound can modulate activation, the channel must be exposed to an activator. In the method of the invention, a lower alkyl phenol is used.

"Lower alkyl phenol" refers to Compound I, which is represented by Formula I:

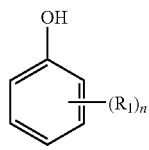

wherein each instance of $R_1$ is independently hydrogen or a $C_{1-6}$ alkyl, and n is an integer from 1-5. Preferred $C_{1-6}$ alkyls include methyl, isopropyl or tertbutyl. Lower alkyl phenols that may be used in the invention include thymol, propofol, 2-tert-butyl-5-methylphenol, 2,5-dimethylphenol, 3,4-dimethylphenol, 0-cresol and 2,6-dimethylphenol.

Detection of TRPA1 Activation

Movement of physiologically relevant substrates through ion channels can be traced by a variety of physical, optical, or chemical techniques (Stein, W. D., *Transport and Diffusion Across Cell Membranes*, 1986, Academic Press, Orlando, Fla.). Assays for modulators of ion channels include electrophysiological assays, cell-by-cell assays using microelectrodes (Wu, C.-F. et al., *Neurosci* 3(9):1888-99 (1983)), i.e., intracellular and patch clamp techniques (Neher, E. and Sakmann, B., *Sci. Amer.* 266:44-51 (1992)), and radioactive tracer ion techniques. Preferably, the effect of the candidate compound is determined by measuring the change in the cell membrane potential after the cell is exposed to the compound. This may be done, for example, using a fluorescent dye that emits fluorescence in response to changes in cell membrane potential and an optical reader to detect this fluorescence.

Optical methods using fluorescence detection are particularly suitable methods for high throughput screening of candidate compounds. Optical methods permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. et al., *Biophys. Acta* 988:319-334 (1989)). Present day optical readers detect fluorescence from multiple samples in a short time and can be automated. Fluorescence readouts are used widely both to monitor intracellular ion concentrations and to measure membrane potentials.

Voltage sensitive dyes have been used to evaluate cellular membrane potential (Zochowski et al., *Biol. Bull.* 198:1-21 (2000)). Membrane potential dyes or voltage-sensitive dyes refer to molecules or combinations of molecules that enter depolarized cells, bind to intracellular proteins or membranes and exhibit enhanced fluorescence. These dyes can be used to detect changes in the activation of an ion channel such as TRPA1, expressed in a cell. Voltage-sensitive dyes include, but are not limited to, modified bisoxonol dyes, sodium dyes, potassium dyes and thorium dyes. The dyes enter cells and bind to intracellular proteins or membranes, therein exhibiting enhanced fluorescence and red spectral shifts (Epps et al., *Chem. Phys. Lipids* 69:137-150 (1994)). Increased depolarization results in more influx of the anionic dye and thus an increase in fluorescence.

In one embodiment, the membrane potential dyes are FMP dyes available from Molecular Devices (Catalog Nos. R8034, R8123). In other embodiments, suitable dyes could include dual wavelength FRET-based dyes such as DiSBAC2, DiSBAC3, and CC-2-DMPE (Invitrogen Cat. No. K1016). [Chemical Name Pacific Blue™ 1,2-ditetradecanoyl-sn-glycero-3-phosphoethanolamine, triethylammonium salt].

Calcium-sensitive fluorescent agents are also useful to detect changes in TRPA1 activation. Suitable types of calcium-sensitive fluorescent agents include Fluo3, Fluo4, Fluo5, Calcium Green, Calcium Orange, Calcium Yellow, Fura-2, Fura-4, Fura-5, Fura-6, Fura-FF, Fura Red, indo-1, indo-5, BTC (Molecular Probes, Eugene, Oreg.), and FLIPR Calcium3 wash-free dye (Molecular Devices, Sunnyvale Calif.). In one embodiment, the intracellular calcium dye is the FLIPR Calcium 3 dye available from Molecular Devices (Part Number: R8091). Additional calcium-sensitive fluorescent agents known to the skilled artisan are also suitable for use in the claimed assay. The calcium-sensitive fluorescent agents can be hydrophilic or hydrophobic.

Sodium-sensitive fluorescent agents are also useful to detect changes in TRPA1 activation. Suitable types of sodium-sensitive fluorescent agents include CoroNa™ Green, CoroNa™ Red chloride, SBFI, and Sodium Green™ (Molecular Probes, Eugene, Oreg.). Additional sodium-sensitive fluorescent agents known to the skilled artisan are also suitable for use in the claimed assay. The sodium-sensitive fluorescent agents can be hydrophilic or hydrophobic.

The voltage- or ion-sensitive fluorescent dyes are loaded into the cytoplasm by contacting the cells with a solution comprising a membrane-permeable derivative of the dye. However, the loading process may be facilitated where a more hydrophobic form of the dye is used. Thus, voltage—and ion-sensitive fluorescent dyes are known and available as hydrophobic acetoxymethyl esters, which are able to permeate cell membranes more readily than the unmodified dyes. As the acetoxymethyl ester form of the dye enters the cell, the ester group is removed by cytosolic esterases, thereby trapping the dye in the cytosol.

The TRPA1 cells of the assay are preloaded with the fluorescent dyes for 30-240 minutes prior to addition of candidate compounds. Preloading refers to the addition of the fluorescent dye for a period prior to candidate compound addition during which the dye enters the cell and binds to intracellular lipophilic moieties. Cells are typically treated with 1 to 10 μM buffered solutions of the dye for 20 to 60 minutes at 37° C. In some cases it is necessary to remove the dye solutions from the cells and add fresh assay buffer before proceeding with the assay.

Another method for testing ion channel activation is to measure changes in cell membrane potential using the patch-clamp technique. (Hamill et al., *Nature* 294:462-4 (1981)). In this technique, a cell is attached to an electrode containing a micropipette tip which directly measures the electrical conditions of the cell. This allows detailed biophysical characterization of changes in membrane potential in response to various stimuli. Thus, the patch-clamp technique can be used as a screening tool to identify compounds that modulate activation of ion channels.

Radiotracer ions have been used for biochemical and pharmacological investigations of channel-controlled ion translocation in cell preparations (Hosford, D. A. et al., *Brain Res.* 516:192-200 (1990)). In this method, the cells are exposed to a radioactive tracer ion and an activating ligand for a period of time, the cells are then washed, and counted for radioactive content. Radioactive isotopes are well known (Evans, E. A., Muramtsu, M. *Radiotracer Techniques and Applications*, M. Dekker, New York (1977)) and their uses have permitted detection of target substances with high sensitivity.

Assay Detection

Detecting and recording alterations in the spectral characteristics of the dye in response to changes in membrane potential may be performed by any means known to those skilled in the art. As used herein, a "recording" refers to collecting and/or storing data obtained from processed fluorescent signals, such as are obtained in fluorescent imaging analysis.

In some embodiments, the assays of the present invention are performed on isolated cells using microscopic imaging to detect changes in spectral (i.e., fluorescent) properties. In other embodiments, the assay is performed in a multi-well format and spectral characteristics are determined using a microplate reader.

By "well" it is meant generally a bounded area within a container, which may be either discrete (e.g., to provide for an isolated sample) or in communication with one or more other bounded areas (e.g., to provide for fluid communication between one or more samples in a well). For example, cells grown on a substrate are normally contained within a well that may also contain culture medium for living cells. Substrates can comprise any suitable material, such as plastic, glass, and the like. Plastic is conventionally used for maintenance and/or growth of cells in vitro.

A "multi-well vessel", as noted above, is an example of a substrate comprising more than one well in an array. Multi-well vessels useful in the invention can be of any of a variety of standard formats (e.g., plates having 2, 4, 6, 24, 96, 384, or 1536, etc., wells), but can also be in a non-standard format (e.g., plates having 3, 5, 7, etc., wells).

A suitable configuration for single cell imaging involves the use of a microscope equipped with a computer system. One example of such a configuration, ATTO's Attofluor™ RatioVision™ real-time digital fluorescence analyzer from Carl Zeiss, is a completely integrated work station for the analysis of fluorescent probes in living cells and prepared specimens (ATTO, Rockville, Md.). The system can observe ions either individually or simultaneously in combinations limited only by the optical properties of the probes in use. The standard imaging system is capable of performing multiple dye experiments such as FMP (for sodium) combined with GFP (for transfection) in the same cells over the same period of time. Ratio images and graphical data from multiple dyes are displayed online.

When the assays of the invention are performed in a multi-well format, a suitable device for detecting changes in spectral qualities of the dyes used is a multi-well microplate reader. Suitable devices are commercially available, for example, from Molecular Devices (FLEXstation™ microplate reader and fluid transfer system or FLIPR™ system), from Hamamatsu (FDSS 6000) and the "VIPR" voltage ion probe reader (Aurora, Bioscience Corp. Calif., USA). The FLIPR-Tetra™ is a second generation reader that provides real-time kinetic cell-based assays using up to 1536 simultaneous liquid transfer systems. All of these systems can be used with commercially available dyes such as FMP, which excites in the visible wavelength range.

Using the FLIPR™ system, the change in fluorescent intensity is monitored over time and is graphically displayed as shown, for example in FIG. 1A. The addition of TRPA1 activating compounds, for example lower alkyl phenols, causes an increase in fluorescence, while compounds that block or inhibit lower alkyl phenol activation of TRPA1 block this increase.

Several commercial fluorescence detectors are available that can inject liquid into a single well or simultaneously into multiple wells. These include, but are not limited to, the Molecular Devices FlexStation (eight wells), BMG NovoStar (two wells) and Aurora VIPR (eight wells). Typically, these instruments require 12 to 96 minutes to read a 96-well plate in flash luminescence or fluorescence mode (1 min/well). An alternative method is to inject the modulator into all sample wells at the same time and measure the luminescence in the whole plate by imaging with a charge-coupled device (CCD) camera, similar to the way that calcium responses are read by calcium-sensitive fluorescent dyes in the FLIPR®, FLIPR-384 or FLIPR-Tetra™ instruments. Other fluorescence imaging systems with integrated liquid handling are expected from other commercial suppliers such as the second generation LEADSEEKER from Amersham, the Perkin Elmer Cell-Lux—Cellular Fluorescence Workstation and the Hamamatsu FDSS6000 System. These instruments can generally be configured to proper excitation and emission settings to read FMP dye ($540_{ex} \pm 15$ nm, $570_{em} \pm 15$ nm). The excitation/emission characteristics differ for each dye, therefore, the instruments are configured to detect the dye chosen for each assay. Selection of appropriate dye and configuration of the instruments to detect the dye chosen for each experiment is within the skill of the artisan practicing the experiments.

Candidate Compounds

Candidate compounds employed in the screening methods of this invention include for example, without limitation, synthetic organic compounds, chemical compounds, naturally occurring products, polypeptides and peptides, nucleic acids, etc.

Essentially any chemical compound can be used as a potential modulator or ligand in the assays of the invention. Most often compounds dissolved in aqueous or organic (especially dimethyl sulfoxide- or DMSO-based) solutions are used. The assays are designed to screen large chemical libraries by automating the assay steps. The compounds are provided from any convenient source to the cells. The assays are typically run in parallel (e.g., in microtiter formats on microtiter plates in robotic assays with different candidate compounds in different wells on the same plate). It will be appreciated that there are many suppliers of chemical compounds, including ChemDiv (San Diego, Calif.), Sigma-Aldrich (St. Louis, Mo.), Fluka Chemika-Biochemica-Analytika (Buchs Switzerland) and the like.

In one embodiment, the screening methods involve providing a small organic molecule or peptide library containing a large number of potential modulators of lower alkyl phenol activation of TRPA1. Such "chemical libraries" are then screened in one or more assays, as described herein, to identify those library members (particular chemical species or subclasses) that display a desired characteristic activity. The compounds thus identified can serve as conventional "lead compounds" or can themselves be used as potential or actual products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14:309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.; etc.).

Candidate agents, compounds, drugs, and the like encompass numerous chemical classes, though typically they are organic molecules, preferably small organic compounds having a molecular weight of more than 100 and less than about 10,000 daltons, preferably, less than about 2000 to 5000 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate compounds may comprise cyclical carbon or heterocyclic structures, and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

A variety of other reagents may be included in the screening assay according to the present invention. Such reagents include, but are not limited to, salts, solvents, neutral proteins, e.g. albumin, detergents, etc., which may be used to facilitate optimal protein-protein binding and/or to reduce non-specific or background interactions. Examples of solvents include, but are not limited to, dimethyl sulfoxide (DMSO), ethanol and acetone, and are generally used at a concentration of less than or equal to 1% (v/v) of the total assay volume. In addition, reagents that otherwise improve the efficiency of the assay, such as protease inhibitors, anti-microbial agents, etc. may be used. Further, the mixture of components in the method may be added in any order that provides for the requisite binding.

The compounds identified using the disclosed assay are potentially useful as ingredients or flavorants in ingestible compositions, i.e., foods and beverages as wells as orally administered medicinals, including mouthwash and toothpaste. Compounds that modulate the burning taste perception associated with lower alkyl phenols are useful as additional ingredients in compositions comprising a lower alkyl phenol. The amount of such a modulating compound will be an amount that yields the desired degree of modulated taste perception of which starting concentrations may generally be between 0.001 and 10000 μM.

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

EXAMPLES

Example 1

Imaging-Based Screening Assay of hTRP1 Expressing HEK293 Cells

As described in greater detail below, HEK 293 cells transfected with a plasmid bearing the human TRPA1 gene, were used to develop the screening assay. As described below, the HEK293 cells were either stably or transiently transfected.

Plasmid Construction

First strand hTRPA1 cDNA was synthesized by Thermoscript RT-PCR System (Invitrogen) from human lung poly A+ RNA (BD Biosciences). The full length hTRPA1 was amplified by PCR with Kpn1 and Xho1 restriction enzyme sites being introduced at the 3' and 5' ends, respectively, using GC Melt (BD Biosciences). The product was PCR purified by Pure Link PCR Purification (Invitrogen) and inserted into the pENTR3C vector (Invitrogen).

After sequencing, 4 mutations were found and the mutations were corrected using the Quick Change Multi Site Directed Mutagenesis Kit (Stratagene).

Finally, LR Recombination Reaction (Invitrogen) was used to insert the entry clone into destination vectors of interest (e.g., pT-Rex-DEST 30, pcDNA-DEST 53, pcDNA 3.2/v5-DEST and pcDNA 6.2/V5-DEST).

Transfection

HEK 293 cells were either transiently or stably transfected with TRPA1 cDNA. For transient transfection, $1.0 \times 10^6$ HEK 293 cells (ATCC) were plated in each well of a 6-well tissue culture dish overnight. The following day, cells were transfected with 4 μg of a pcDNA3.2 vector containing TRPA1 cDNA and 8 μl of Lipofectamine 2000 (Invitrogen), according to the manufacturer's protocol, and incubated overnight. The following day, transfected cells were trypsinized and seeded into 96-well black, clear bottom, poly-D-lysine plates (Corning) at a density of 70,000 cells/well in a 100 µl volume and incubated in a 37° C./5% $CO_2$ incubator overnight.

Stable clones were generated by transfecting $1.0 \times 10^6$ HEK 293 cells with 4 µg of pcDNA 3.2-TRPA1 in a 35 mm tissue culture dish using the transfection method described above. Two days post-transfection, the cells were trypsinized and diluted 1:10 and 1:100 in growth medium containing 1 mg/ml Geneticin (Invitrogen) to select for single clones. Cells were maintained in this medium until single individual clones could be isolated and expanded. Upon selection of individual clones, cells were maintained in medium containing 0.25 mg/ml Geneticin to maintain the selective pressure. Individual clones were then examined with membrane potential dye in the FLEXstation or FLIPR® as described above. Those clones with the largest fluorescent response to cinnamaldehyde were then selected and examined for further analysis. Selected clones with the highest $EC_{50}$ to cinnamaldehyde were then expanded and used for the screening assays.

Membrane Potential Assay

Once expression of TRPA1 was confirmed, 100 µl of the Blue or Red FMP dye (Molecular Devices) was added to each well of plates seeded with the transiently transfected cells. The plate was then incubated in a 37° C./5% $CO_2$ incubator for 1 hour. The plate was read in a FLEXStation microplate reader (Molecular Devices) with an excitation of 530 nm and an emission of 565 nm. The fluorescence was monitored for 3 minutes upon exposure of the cells to a TRPA1 activating agent (e.g., cinnamaldehyde).

Example 2

Imaging-Based Screening Assay of hTRP1 Expressing HEK293 Cells in the Presence of Lower Alkyl Phenol Compounds Demonstration of TRPA1 response to the lower alkyl phenol, thymol is shown in FIG. 1A. FIG. 1A shows fluorescence data collected for cells stably transfected with a plasmid containing the hTRPA1 gene as described above. Fluorescence data for parental HEK293 cells was also collected (FIG. 1B).

HEK 293 cells stably expressing TRPA1 were loaded with FMP dye, and then treated with lower alkyl phenol compounds and monitored for an increase in cellular fluorescence in the FLEXstation. Samples in a 384-well plate were evaluated in a 5 minute assay on the FLIPR-Tetra™ (Molecular Devices). The assay was performed on a FLIPR™ using the excitation 510-545 nm and emission 565-625 nm filter sets. TRPA1-Transfected HEK cells, 15,000/well, were seeded overnight on poly-D-lysine coated 384 well plates in 20 µl media. Membrane Potential Assay Dye Red (Molecular Devices), 20 µl/well, was added and the plates incubated for 1 hour in a 37° C. and 5% $CO_2$ incubator. The plates were then removed from the incubator and equilibrated to room temperature for 15 minutes before reading on the FLIPR®. The plates were read on the FLIPR® for a total of 3 minutes. Baseline fluorescence was obtained on the FLIPR® for 10 seconds followed by addition (typically 10 µl) of each agonist by the FLIPR® and read for an additional 2 minutes and 50 seconds.

An increase in fluorescence of the membrane potential sensitive dye corresponds to an increase activation of an hTRPA1 ion channel. FIG. 1A shows an increase in fluorescence of the membrane potential sensitive dye and thus, an increase activation of the TRPA1 ion channel upon addition of thymol (arrow). The addition of thymol (arrow) produces no change in fluoresce in parental cells not expressing TRPA1 (FIG. 1B).

FIG. 2A shows that the fluorescence of the membrane potential dye in the cells expressing hTRPA1 increases in a dose dependant manner as the concentration of thymol present increases. The fluorescence of the membrane potential dye in parental HEK293 cells does not show the same thymol dose response. FIG. 2A indicates that thymol activates TRPA1 with an $EC_{50}$ of about 2 µM.

FIG. 3 shows that thymol stimulates TRPA1 to the same extent and the known activator of TRPA1, cinnamaldehyde. Cells expressing TRPA1 were subjected to the fluorescence assay described above in the presence of either thymol or cinnamaldehyde. FIG. 3A indicates that thymol stimulates TRPA1 activation at a level similar to that of cinnamaldehyde. Cells not expressing TRPA1 show no change in activation upon addition of thymol or cinnamaldehyde. FIG. 3B shows the level of activation of TRPA1 in the presence of either thymol or cinnamaldehyde over cells not expressing TRPA1. At 10 µM, thymol induced activation of TRPA1 that was about 7 fold higher than the standard value obtained from cells not expressing TRPA1.

FIG. 4 provides fluorescence data for cells exposed to one of o-Cresol-MP, 2,5-Dimethylphenol-MP, 2,6-Dimethylphenol-MP, 3,4-Dimethylphenol-MP, 2-tert-Butyl-5-methylphenol-MP and Propofol-MP. FIG. 4 indicates that all phenolic compounds tested on TRPA1 transfected cells generated an increase in relative fluorescence of the membrane potential sensitive dye as the concentration of phenolic compound increased. Parental HKE293 cells produced no response when treated with o-Cresol-MP, 2,5-Dimethylphenol-MP, 2,6-Dimethylphenol-MP, and 3,4-Dimethylphenol-MP, however, background fluorescence was observed in parental cells treated with 2-tert-Butyl-5-methylphenol-MP and Propofol-MP at higher concentrations. (FIG. 4).

Example 3

Assay to Demonstrate that Activation is Via TRPA1

FIG. 5 shows the results of siRNA experiments performed to confirm that the thymol response occurs via TRPA1. The ideal modulating compound would modulate TRPA1 but not other channels.

HEK293 cells were transiently transfected with one of siRNA for hTRPA1, and one of Silencer pre-designed and validated siRNA (Ambion), GAPDH or negative siRNA control. $1 \times 10^6$ hTRPA1 stably transfected HEK 293 cells were plated in 35 mm dishes overnight. The next day 10 µM of each siRNA was transfected into these cells using siPORT Amine (Ambion) and incubated overnight. The following day, transfected cells were trypsinized and seeded into 384-well black, clear bottom, poly-D-lysine plates (Corning) at a density of 15,000 cells/well in a 20 µl volume and incubated in a 37° C./5% $CO_2$ incubator overnight.

The cells were then loaded with membrane potential sensitive dye and subjected to the fluorescence assay described in Example 2. Fluorescence was measure in the presence of increasing concentrations of each of cinnamaldehyde and thymol. FIG. 5A shows that in the presence of increasing concentrations of cinnamaldehyde, the fluorescence of cells transfected with hTRPA1 siRNA molecules did not increase as much as the fluorescence of cells transfected with GAPDH, or the negative siRNA control. FIG. 5B shows that in the presence of increasing concentrations of thymol, the fluorescence of cells transfected with hTRPA1 siRNA molecules did not increase as much as the fluorescence of cells transfected with GAPDH or the negative siRNA control. Thus, interfering with the expression of TRPA1 caused a decrease in the cells response to each of cinnamaldehyde and thymol. The drop in the thymol and cinnamaldehyde response corresponds to a drop in expression of TRPA1. This indicates that the cinnamaldehyde and thymol response observed is dependant on the expression of hTRPA1 and thus, is specific to TRPA1.

FIG. 6 indicates that the lower alkyl phenol compounds tested selectively activate TRPA1 versus other TRP channels. FIG. 6 indicates that the phenol does not selectively activate TRPA1. Rather phenol activates TRPV1.

HEK293 cells were stably transfected with one of hTRPA1, hTRPV1 or hTRPM5. CHO cells were stably transfected with one of hTRPM4B or TRPM5. Parental HEK293 and CHO cells were also used as a negative control. The cells were loaded with FMP dye, and then treated with lower alkyl phenol compounds and monitored for an increase in cellular fluorescence in the FLIPR using the protocol outlined in Example 2.

FIG. 6A indicates that HEK293 cells expressing hTRPA1 generated an increase in relative fluorescence of the membrane potential sensitive dye as the concentration of propofol increased. Cells expressing hTRPV1, hTRPM4B or hTRPM5 did not generate the same increase in relative fluorescence of the membrane potential sensitive dye as the concentration of propofol increased.

FIG. 6B indicates that HEK293 cells expressing hTRPA1 generated an increase in relative fluorescence of the membrane potential sensitive dye as the concentration of 2-tert-butyl-5-methylphenol increased. Cells expressing hTRPV1, hTRPM4B or hTRPM5 did not generate the same increase in relative fluorescence of the membrane potential sensitive dye as the concentration of 2-tert-butyl-5-methylphenol increased.

FIG. 6C indicates that HEK293 cells expressing hTRPA1 generated an increase in relative fluorescence of the membrane potential sensitive dye as the concentration of thymol increased. Cells expressing hTRPV1, hTRPM4B or hTRPM5 did not generate the same increase in relative fluorescence of the membrane potential sensitive dye as the concentration of thymol.

FIG. 6D indicates that HEK293 cells expressing hTRPA1 generated an increase in relative fluorescence of the membrane potential sensitive dye as the concentration of 2,5-dimethylphenol increased. Cells expressing hTRPV1, hTRPM4B or hTRPM5 did not generate the same increase in relative fluorescence of the membrane potential sensitive dye as the concentration of 2,5-dimethylphenol increased.

FIG. 6E indicates that HEK293 cells expressing hTRPA1 generated an increase in relative fluorescence of the membrane potential sensitive dye as the concentration of 2,6-dimethylphenol increased. Cells expressing hTRPV1, hTRPM4B or hTRPM5 did not generate the same increase in relative fluorescence of the membrane potential sensitive dye as the concentration of 2,6-dimethylphenol increased.

FIG. 6F indicates that HEK293 cells expressing hTRPA1 generated an increase in relative fluorescence of the membrane potential sensitive dye as the concentration of 3,4-dimethylphenol increased. Cells expressing hTRPV1, hTRPM4B or hTRPM5 did not generate the same increase in relative fluorescence of the membrane potential sensitive dye as the concentration of 3,4-dimethylphenol increased.

FIG. 6G indicates that HEK293 cells expressing hTRPA1 generated an increase in relative fluorescence of the membrane potential sensitive dye as the concentration of o-Cresol increased. Cells expressing hTRPV1, hTRPM4B or hTRPM5 did not generate the same increase in relative fluorescence of the membrane potential sensitive dye as the concentration of o-Cresol increased.

FIG. 6H indicates that HEK293 cells expressing hTRPV1 generated an increase in relative fluorescence of the membrane potential sensitive dye as the concentration of phenol increased. Cells expressing hTRPA1, hTRPM4B or hTRPM5 did not generate the same increase in relative fluorescence of the membrane potential sensitive dye as the concentration of phenol increased.

Example 4

Structure-Activity Relationship of Phenolic Compounds that Activate TRPA1

Table 1 shows the structure of the lower alkyl phenol compounds that activate TRPA1 ion channel along with each compound's $EC_{50}$.

TABLE 1

Structures and $EC_{50}$ Values for TRPA1 Activation* by Lower Alkyl Phenol Compounds.

| Name | Structure | $EC_{50}$ (μM) ± SEM (n = 4) |
|---|---|---|
| Propofol | 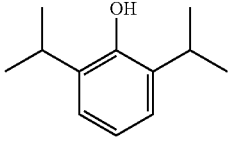 | 13 ± 6 |
| 2-tert-butyl-5-methylphenol | 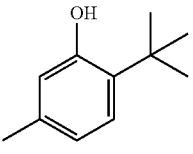 | 4 ± 2 |
| Thymol | 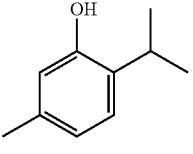 | 12 ± 6 |
| 2,5-dimethylphenol | 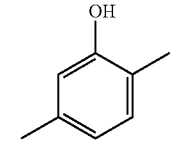 | 52 ± 29 |
| 2,6-dimethylphenol | 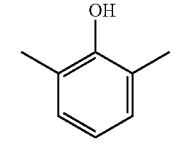 | 66 ± 22 |
| 3,4-dimethylphenol | 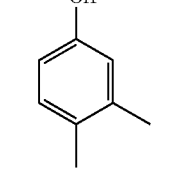 | 123 ± 27 |

TABLE 1-continued

Structures and EC$_{50}$ Values for TRPA1 Activation*
by Lower Alkyl Phenol Compounds.

| Name | Structure | EC$_{50}$ (μM) ± SEM (n = 4) |
|---|---|---|
| o-Cresol | OH (structure) | 327 ± 132 |

*EC$_{50}$ for cinnamaldehyde standard was 7 ± 2 μM

HEK293 cells stably transfected with hTRPA1 were loaded with FMP dye, and then treated with lower alkyl phenol compounds and monitored for an increase in cellular fluorescence in the FLIPR using the protocol outlined in Example 2.

Table 1 provides the EC$_{50}$ of the lower alkyl phenol compounds tested. While each of the lower alkyl phenol compounds tested activated TRPA1, Propfol, 2-tert-Butyl-5-methylphenol, thymol and 2,5, Dimethylphenol more potently activated TRPA1 than 3,4-dimethylphenol, O-Cresol or 2,6-dimethylphenol.

Example 5

Assay to Screen and Identify Compounds that Modulate Lower Alkyl Phenol-Stimulated TRPA1

The ability of compounds to modulate the TRPA1 lower alkyl phenol response were identified using the assay protocol described above in Example 2. In this assay, rather than measuring TRPA1 activation in the presence of a lower alkyl phenol alone, TRPA1 activation is measured in the presence of a lower alkyl phenol and a candidate compound. The lower alkyl phenol and candidate compound can be present in the assay at the same time or one after the other. If present at the same time, absence of lower alkyl phenol activation of TRPA1 indicates that the candidate compound can modulate lower alkyl phenol activation of TRPA1. If TRPA1 activation is measured in the presence of the lower alkyl phenol and then the candidate compound is added, a change in TRPA1 activation upon addition of the candidate compound indicates that the candidate compound can modulate lower alkyl phenol activation of TRPA1. If TRPA1 activation is measured in the presence of the candidate compound and then the lower alkyl phenol compound is added, a change in TRPA1 activation upon addition of the candidate compound indicates that the candidate compound does not modulate lower alkyl phenol activation of TRPA1. However, no change in fluorescence upon addition of the lower alkyl phenol compound indicates that the candidate compound does modulate lower alkyl phenol activation of TRPA1. Appropriate control experiments are performed and can easily be determined by the skilled artisan.

FIG. 7 indicates that thymol stimulation of TRPA1 is selectively blocked by camphor. HEK293 cells and CHO cells expressing TRPA1 were subjected to the assay described in Example 2. The cells were pretreated with camphor and then treated with either thymol or cinnamaldehyde. FIG. 7 indicates that camphor completely blocked thymol stimulation of TRPA1. The IC$_{50}$ in HEK293 cells is 300 μM and in CHO cells is 150 μM.

FIGS. 8 and 9 demonstrate the assay for screening candidate modulator compounds described in this Example. Specifically, FIG. 8 indicates that camphorquinone triggers an agonist response in TRPA1 transfected HEK293 cells and desensitizes thymol and cinnamaldehyde responses. FIGS. 8A and 8B show FLIPR traces with treatment of cells with camphorquinone and then TRPA1 agonists thymol (8A) or cinnamaldehyde (8B). Response curves show camphorquinone inhibition via desensitization of thymol (8C) or cinnamaldehyde (8D) responses.

FIG. 9 provides a dose response curve of TRPA1 activation to the modulating compounds camphor, camphorquinone, camphoric acid and limonene. HEK293 cells stably transfected with hTRPA1 were loaded with FMP dye, and then treated with camphor, camphorquinone, camphoric acid or limonene and monitored for an increase in cellular fluorescence in the FLEXstation using the protocol outlined in Example 2. FIG. 9 indicates that camphor, camphorquinone, camphoric acid and limonene are TRPA1 agonists.

FIG. 10 provides a dose response curve of TRPA1 activation to the isomers of pinanediol. HEK293 cells stably transfected with hTRPA1 were loaded with FMP dye. Pinanediol +/− isomers were added to the cells followed by the addition of 10 μM thymol. Cellular fluorescence was measured in the FLIPR using the protocol outlined in Example 2. FIG. 10 demonstrates that unexpectedly, pinanediol exhibits inhibitory activity, albeit weak, for thymol activation.

FIG. 11 provides the structures and compounds that act as agonists of thymol activation of TRPA1, and of compounds that have agonist activity, but do not act as agonists of thymol activation of TRPA1. Specifically, camphor and pinanediol are agonists of thymol activation of TRPA1, whereas camphorquinone, camphoric acid, camphorsufomamide and limonene have agonist activity, but do not act as agonists of thymol activation of TRPA1.

The above Examples describe an assay that is used to demonstrate that hTRPA1 is activated by lower alkyl phenol compounds, including thymol. The assay is further used to identify compounds that are capable of modulating the activation of hTRPA1 by lower alkyl phenol compounds. The assay can be used to identify compounds that are capable of inhibiting the activation of hTRPA1 by thymol. The pungent taste sensation associated with thymol decreases patient compliance with treatments that have thymol as an ingredient. The pungent taste of thymol is sensed because of thymol activation of the TRPA1 ion channel. The compounds that can inhibit thymol activation of TRPA1, which are identified using the assay described herein are therefore useful to prevent to pungent taste sensation of thymol and will consequently aid in increasing patient compliance with treatments that have thymol as an ingredient. Accordingly, the assay described herein is useful to identify compounds that can inhibit thymol activation of TRPA1, and as a result, decrease or mask completely the pungent taste associated with thymol.

Example 6

Assay to Screen and Identify Compounds that Cause Taste Aversion in Mice

In this assay, the ability of identified lower alkyl phenols to evoke taste aversion in mice was measured. Mice were exposed to increasing concentrations of lower alkyl phenols. The number of times that a given animal licked solutions of lower alkyl phenol compounds was recorded.

FIG. 12 indicates that all of the lower alkyl phenols were able to evoke taste aversion in mice at mM concentrations.

Phenol had the highest measured $EC_{50}$ value of 35 mM. 2,6-isopropylphenol had the lowest measured $EC_{50}$ value of 0.194 mM.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All publications, patents and patent applications cited herein are incorporated by reference in their entirety into the disclosure.

What is claimed is:

1. A method for screening a candidate compound to identify a compound that modulates activation of full-length human TRPA1 by thymol, said method comprising:
   (i) measuring the level of activation of thymol-activated-full-length human TRPA1 in the presence of a candidate compound to obtain a measured value; and
   (ii) comparing said measured value to a standard value, wherein a difference between the measured value and the standard value indicates that the candidate compound modulates thymol-activation of full-length human TRPA1,
wherein the standard value is the value determined by measurement, in the absence of the candidate compound, of the level of activation of thymol-activated full-length human TRPA1.

2. The method of claim 1, wherein a difference between the level of activation of the thymol-activated full-length human TRPA1 in the presence of the candidate compound, and the standard value, provides a quantitative measure of modulation of the level of activation of full-length human TRPA1.

3. The method of claim 1, wherein the level of activation of thymol-activated full-length human TRPA1 is determined by measuring the flux of ions into or out of a full-length human TRPA1 expressing cell in the presence of thymol.

4. The method of claim 3, wherein the flux of ions is measured using an indicator capable of producing a signal that signifies the movement of ions into or out of a cell.

5. The method of claim 4, wherein the indicator is selected from the group consisting of calcium sensitive fluorescent dyes, sodium-sensitive fluorescent dyes, membrane potential-sensitive fluorescent dyes and mixtures thereof.

6. The method of claim 5, wherein the indicator is in acetoxymethyl ester form.

7. The method of claim 3, wherein the cells are selected from a group comprising HEK 293, CHO, COS-7, HeLa, PC-12, and BA, or mixtures thereof.

8. The method of claim 3, wherein the cells are HER 293 or CHO cells.

9. The method of claim 1, wherein to measure the level of activation full-length human TRPA1, one or more techniques selected from the following group is used: fluorimetry, flow cytometry, fluorescent microscopy, fluorescent imaging plate reading or patch clamp technique.

10. The method of claim 1, wherein to measure the level of activation full-length human TRPA1 a fluorescent imaging plate reader is used.

11. The method of claim 1, wherein the full-length human TRPA1 is expressed in cells maintained in a culture vessel having a single compartment.

12. The method of claim 1, wherein the full-length human TRPA1 is expressed in cells maintained in a divided culture vessel having an array of individual compartments.

13. The method of claim 12, wherein a candidate compound is added to more than one compartment at a time.

14. The method of claim 12, wherein said measuring is effected in more than one compartment at a time.

15. A method for identifying a compound that modulates the activation of full-length human TRPA1 by thymol, said method comprising:
   (a) incubating cells expressing full-length human TRPA1 with an indicator for a time sufficient to allow incorporation of the indicator into the cells, wherein the indicator is capable of signaling activation of full-length human TRPA1;
   (b) incubating said cells with a candidate compound while maintaining said cells in a solution that contains thymol and is suitable to allow a flux of ions through full-length human TRPA 1;
   (c) after completing steps (a) and (b), measuring a signal from the indicator in the presence of the candidate modulator compound; and
   (d) comparing the signal of step (c) to a standard value, wherein the indicator indicates the flux of ions via thymol-activated full-length human TRPA1 and a difference between the signal of step (c) and the standard value indicates that the candidate compound modulates full-length human TRPA1 activation,
wherein the standard value is the value determined by measurement, in the absence of a candidate compound, of the level of activation of thymol-activated full-length human TRPA1.

16. The method of claim 15, wherein a difference in the level of activation of thymol-activated full-length human TRPA1 in the presence of candidate compound, compared to the standard, provides a quantitative measure of modulation of the level of activation full-length human TRPA1.

17. The method of claim 15, wherein the level of activation of thymol-activated full-length human TRPA1 is determined by measuring the flux of ions into or out of a full-length human TRPA1-expressing cell in the presence of thymol.

18. The method of claim 17, wherein the flux of ions is measured using an indicator capable of producing a signal that signifies the movement of ions into or out of a cell.

19. The method of claim 18, wherein the indicator is selected from the group consisting of calcium-sensitive fluorescent dyes, sodium-sensitive fluorescent dyes, membrane potential-sensitive fluorescent dyes and mixtures thereof.

20. The method of claim 19, wherein the indicator is in acetoxymethyl ester form.

21. The method of claim 15, wherein the cells are selected from a group comprising HEK 293, CHO, COS-7, HeLa, PC-12, and BA, or mixtures thereof.

22. The method of claim 21, wherein the cells are HEK 293 or CHO cells.

23. The method of claim 15, wherein to measure the level of activation TRPA1, one or more techniques selected from the following group is used: fluorimetry, flow cytometry, fluorescent microscopy, fluorescent imaging plate reading or patch clamp technique.

24. The method of claim 15, wherein the measuring is performed by a fluorescent imaging plate reader.

25. The method of claim 15, wherein the cells are maintained in a culture vessel having a single compartment.

26. The method of claim 15, wherein the cells are maintained in a divided culture vessel having an array of individual compartments.

27. The method of claim 26, wherein a candidate compound is added to more than one compartment at a time.

28. The method of claim 26, wherein said measuring is effected in more than one compartment at a time.

* * * * *